US012533240B2

(12) United States Patent
Hutton et al.

(10) Patent No.: US 12,533,240 B2
(45) Date of Patent: Jan. 27, 2026

(54) DRIVE INSTRUMENTS WITH RETENTION MECHANISMS, MEDICAL IMPLANTS, AND RELATED TECHNOLOGIES

(71) Applicant: Amplify Surgical, Inc., Irvine, CA (US)

(72) Inventors: Clark Hutton, Carlsbad, CA (US); Pako Barba, San Diego, CA (US)

(73) Assignee: Amplify Surgical, Inc., Foothill Ranch, CA (US)

( * ) Notice: Subject to any disclaimer, the term of this patent is extended or adjusted under 35 U.S.C. 154(b) by 225 days.

(21) Appl. No.: 18/464,949

(22) Filed: Sep. 11, 2023

(65) Prior Publication Data

US 2025/0082478 A1 Mar. 13, 2025

Related U.S. Application Data

(63) Continuation of application No. PCT/US2022/019706, filed on Mar. 10, 2022.

(Continued)

(51) Int. Cl.

| | |
|---|---|
| ***A61F 2/46*** | (2006.01) |
| ***A61F 2/44*** | (2006.01) |
| *A61F 2/30* | (2006.01) |

(52) U.S. Cl.

CPC .......... *A61F 2/4425* (2013.01); *A61F 2/4611* (2013.01); *A61F 2002/30507* (2013.01);

(Continued)

(58) Field of Classification Search

CPC ....... A61F 2/4455; A61F 2/447; A61F 2/4611

See application file for complete search history.

(56) References Cited

U.S. PATENT DOCUMENTS

| | | | |
|---|---|---|---|
| 619,413 | A | 2/1899 | Higgins |
| 3,486,505 | A | 12/1969 | Morrison |

(Continued)

FOREIGN PATENT DOCUMENTS

| | | |
|---|---|---|
| AU | 2013206287 | 7/2013 |
| AU | 2013262504 | 1/2015 |

(Continued)

OTHER PUBLICATIONS

Choi, Chang Myong et al. "How I do it? Biportal endoscopic spinal surgery (BESS) for treatment of lumbar spinal stenosis." Acta Neurochir (2016) 158:459-463; published Jan. 18, 2016, 5 pages.

(Continued)

*Primary Examiner* — Ellen C Hammond

(74) *Attorney, Agent, or Firm* — Perkins Coie LLP

(57) ABSTRACT

A system for treating a subject's spine can include an intervertebral spacer. The intervertebral spacer can be movable between unexpanded and expanded configurations. A locking member can have a threaded distal region configured to threadably engage the intervertebral spacer, and a proximal drive. A drive instrument assembly can include a retention mechanism detachably couplable to the locking member. The retention mechanism can include a socket configured to receive the drive head to rotationally fix the drive instrument to the locking member, and a spring element biased outwardly to releasably hold the drive head in the socket when the spring element extends into the drive head. The drive instrument assembly can be configured to rotate the locking member to move the intervertebral spacer from the unexpanded configuration to the expanded configuration.

15 Claims, 11 Drawing Sheets

Related U.S. Application Data

(60) Provisional application No. 63/159,327, filed on Mar. 10, 2021.

(52) U.S. Cl.
CPC ............... *A61F 2002/30565* (2013.01); *A61F 2002/4615* (2013.01); *A61F 2002/4629* (2013.01)

(56) References Cited

U.S. PATENT DOCUMENTS

| | | | |
|---|---|---|---|
| 4,164,225 | A | 8/1979 | Johnson |
| 4,456,005 | A | 6/1984 | Lichty |
| 4,657,550 | A | 4/1987 | Daher |
| 4,834,757 | A | 5/1989 | Brantigan |
| 4,858,601 | A | 8/1989 | Glisson |
| 4,863,476 | A | 9/1989 | Shepperd |
| 5,059,193 | A | 10/1991 | Kuslich |
| 5,171,278 | A | 12/1992 | Pisharodi |
| 5,171,279 | A | 12/1992 | Mathews |
| 5,290,312 | A | 3/1994 | Kojimoto |
| 5,306,310 | A | 4/1994 | Siebels |
| 5,336,223 | A | 8/1994 | Rogers |
| 5,390,683 | A | 2/1995 | Pisharodi |
| 5,405,391 | A | 4/1995 | Hednerson |
| 5,425,772 | A | 6/1995 | Brantigan |
| 5,437,637 | A | 8/1995 | Lieber et al. |
| 5,443,514 | A | 8/1995 | Steffee |
| 5,458,641 | A | 10/1995 | Ramirez |
| 5,554,191 | A | 9/1996 | Lahille |
| 5,571,192 | A | 11/1996 | Schonhoffer |
| 5,609,635 | A | 3/1997 | Michelson |
| 5,653,762 | A | 8/1997 | Pisharodi |
| 5,653,763 | A | 8/1997 | Errico |
| 5,658,335 | A | 8/1997 | Allen |
| 5,665,122 | A | 9/1997 | Kambin |
| 5,690,222 | A | 11/1997 | Peters |
| 5,693,100 | A | 12/1997 | Pisharodi |
| 5,702,455 | A | 12/1997 | Saggar |
| 5,716,415 | A | 2/1998 | Steffee |
| 5,735,290 | A | 4/1998 | Sterman et al. |
| 5,762,629 | A | 6/1998 | Kambin |
| 5,776,198 | A | 7/1998 | Rabbe |
| 5,782,832 | A | 7/1998 | Larsen et al. |
| 5,846,182 | A | 12/1998 | Wolcott |
| 5,865,848 | A | 2/1999 | Baker |
| 5,888,223 | A | 3/1999 | Bray |
| 5,980,522 | A | 11/1999 | Koros |
| 5,989,290 | A | 11/1999 | Biedermann |
| 6,015,436 | A | 1/2000 | Schonhoffer |
| 6,039,761 | A | 3/2000 | Li |
| 6,045,579 | A | 4/2000 | Hochshuler |
| 6,080,193 | A | 6/2000 | Hochshuler |
| 6,093,207 | A | 7/2000 | Pisharodi |
| 6,102,950 | A | 8/2000 | Vaccaro |
| 6,117,174 | A | 9/2000 | Nolan |
| 6,126,689 | A | 10/2000 | Brett |
| 6,126,869 | A | 10/2000 | Haaland |
| 6,129,763 | A | 10/2000 | Chauvin |
| 6,159,244 | A | 12/2000 | Suddaby |
| 6,162,170 | A | 12/2000 | Foley et al. |
| 6,174,334 | B1 | 1/2001 | Suddaby |
| 6,176,881 | B1 | 1/2001 | Schumlaut |
| 6,183,517 | B1 | 2/2001 | Suddaby |
| 6,190,413 | B1 | 2/2001 | Sutcliffe |
| 6,190,414 | B1 | 2/2001 | Young |
| 6,193,756 | B1 | 2/2001 | Studer |
| 6,193,757 | B1 | 2/2001 | Foley |
| 6,193,775 | B1 | 2/2001 | Metz |
| 6,200,348 | B1 | 3/2001 | Biedermann |
| 6,214,050 | B1 | 4/2001 | Huene |
| 6,296,647 | B1 | 10/2001 | Robioneck |
| 6,299,644 | B1 | 10/2001 | Vanderschot |
| 6,332,895 | B1 | 12/2001 | Suddaby |
| 6,348,058 | B1 | 2/2002 | Melkent et al. |
| 6,395,034 | B1 | 5/2002 | Suddaby |
| 6,409,766 | B1 | 6/2002 | Brett |
| 6,413,278 | B1 | 7/2002 | Marchosky |
| 6,419,705 | B1 | 7/2002 | Erickson |
| 6,436,140 | B1 | 8/2002 | Liu |
| 6,454,806 | B1 | 9/2002 | Cohen |
| 6,491,724 | B1 | 12/2002 | Ferree |
| 6,517,543 | B1 | 2/2003 | Berrevoets et al. |
| 6,562,074 | B2 | 5/2003 | Gerbec |
| 6,582,431 | B1 | 6/2003 | Ray |
| 6,641,614 | B1 | 11/2003 | Wagner et al. |
| 6,648,917 | B2 | 11/2003 | Gerbec |
| 6,660,038 | B2 | 12/2003 | Boyer |
| 6,666,891 | B2 | 12/2003 | Boehm |
| 6,685,742 | B1 | 2/2004 | Jackson |
| 6,706,070 | B1 | 3/2004 | Wagner |
| 6,709,458 | B2 | 3/2004 | Michelson |
| 6,723,126 | B1 | 4/2004 | Berry |
| 6,730,126 | B2 | 5/2004 | Boehm |
| 6,746,484 | B1 | 6/2004 | Liu |
| 6,821,298 | B1 | 11/2004 | Jackson |
| 6,833,006 | B2 | 12/2004 | Foley |
| 6,852,129 | B2 | 2/2005 | Gerbec |
| 6,863,673 | B2 | 3/2005 | Gerbec |
| 6,893,464 | B2 | 5/2005 | Kiester |
| 6,921,403 | B2 | 7/2005 | Cragg |
| 6,969,392 | B2 | 11/2005 | Gitis et al. |
| 7,070,598 | B2 | 7/2006 | Lim |
| 7,083,650 | B2 | 8/2006 | Moskowitz et al. |
| 7,087,055 | B2 | 8/2006 | Lim et al. |
| 7,112,222 | B2 | 9/2006 | Fraser et al. |
| 7,217,293 | B2 | 5/2007 | Branch |
| 7,513,900 | B2 | 4/2009 | Carrison |
| 7,625,377 | B2 | 12/2009 | Veldhuizen |
| 7,731,751 | B2 | 6/2010 | Butler et al. |
| 7,799,057 | B2 | 9/2010 | Hudgins et al. |
| 7,799,081 | B2 | 9/2010 | McKinley |
| 7,824,427 | B2 | 11/2010 | Perez-Cruet |
| 7,846,206 | B2 | 12/2010 | Oglaza |
| 7,879,098 | B1 | 2/2011 | Simmons |
| 7,922,729 | B2 | 4/2011 | Michelson |
| RE42,525 | E | 7/2011 | Simonson |
| 8,012,207 | B2 | 9/2011 | Kim |
| 8,016,767 | B2 | 9/2011 | Miles et al. |
| 8,043,334 | B2 | 10/2011 | Fisher et al. |
| 8,062,375 | B2 | 11/2011 | Glerum et al. |
| 8,097,018 | B2 | 1/2012 | Malandain |
| 8,097,035 | B2 | 1/2012 | Glenn |
| 8,109,972 | B2 | 2/2012 | Zucherman |
| 8,110,004 | B2 | 2/2012 | Valdevit |
| 8,152,837 | B2 | 4/2012 | Atarac |
| 8,317,798 | B2 | 11/2012 | Lim |
| 8,323,344 | B2 | 12/2012 | Galley |
| 8,353,963 | B2 | 1/2013 | Glerum |
| 8,382,842 | B2 | 2/2013 | Greenhalgh et al. |
| 8,394,145 | B2 | 3/2013 | Weiman |
| 8,398,713 | B2 | 3/2013 | Weiman |
| 8,409,291 | B2 | 4/2013 | Blackwell |
| 8,425,613 | B2 | 4/2013 | Theofilos |
| 8,435,298 | B2 | 5/2013 | Weiman |
| 8,491,657 | B2 | 7/2013 | Attia |
| 8,491,659 | B2 | 7/2013 | Weiman |
| 8,496,709 | B2 | 7/2013 | Schell |
| 8,506,635 | B2 | 8/2013 | Palmatier |
| 8,512,407 | B2 | 8/2013 | Butler et al. |
| 8,518,120 | B2 | 8/2013 | Glerum et al. |
| 8,541,355 | B2 | 9/2013 | Fleckenstein |
| 8,556,979 | B2 | 10/2013 | Weiman et al. |
| 8,568,317 | B1 | 10/2013 | Gharib et al. |
| 8,568,481 | B2 | 10/2013 | Olmos |
| 8,579,907 | B2 | 11/2013 | Lim |
| 8,628,576 | B2 | 1/2014 | Triplett |
| 8,632,594 | B2 | 1/2014 | Williams et al. |
| 8,632,595 | B2 | 1/2014 | Weiman |
| 8,652,174 | B2 | 2/2014 | Gabelberger |
| 8,663,329 | B2 | 3/2014 | Ernst |
| 8,678,576 | B2 | 3/2014 | Edombingo |
| 8,679,183 | B2 | 3/2014 | Glerum et al. |

(56) References Cited

U.S. PATENT DOCUMENTS

| | | | |
|---|---|---|---|
| 8,685,095 | B2 | 4/2014 | Miller |
| 8,685,098 | B2 | 4/2014 | Glerum et al. |
| 8,709,086 | B2 | 4/2014 | Glerum |
| 8,777,993 | B2 | 7/2014 | Siegal |
| 8,778,027 | B2 | 7/2014 | Medina |
| 8,808,385 | B1 | 8/2014 | Smith |
| 8,845,731 | B2 | 9/2014 | Weiman |
| 8,845,732 | B2 | 9/2014 | Weiman |
| 8,845,734 | B2 | 9/2014 | Weiman |
| 8,852,279 | B2 | 10/2014 | Weiman |
| 8,864,833 | B2 | 10/2014 | Glerum et al. |
| 8,888,853 | B2 | 11/2014 | Glerum et al. |
| 8,888,854 | B2 | 11/2014 | Glerum et al. |
| 8,900,305 | B2 | 12/2014 | Stad |
| 8,926,704 | B2 | 1/2015 | Glerum et al. |
| 8,940,048 | B2 | 1/2015 | Butler et al. |
| 8,986,386 | B2 | 3/2015 | Oglaza et al. |
| 8,986,387 | B1 | 3/2015 | To et al. |
| 9,034,041 | B2 | 5/2015 | Wolters et al. |
| 9,039,771 | B2 | 5/2015 | Glerum et al. |
| 9,044,342 | B2 | 6/2015 | Perloff et al. |
| 9,060,876 | B1 | 6/2015 | To et al. |
| 9,078,769 | B2 | 7/2015 | Farin |
| 9,119,730 | B2 | 9/2015 | Glerum et al. |
| 9,125,757 | B2 | 9/2015 | Weiman |
| 9,149,367 | B2 | 10/2015 | Davenport et al. |
| 9,155,628 | B2 | 10/2015 | Glerum et al. |
| 9,186,258 | B2 | 11/2015 | Davenport et al. |
| 9,198,765 | B1 | 12/2015 | Pimenta |
| 9,198,772 | B2 | 12/2015 | Weiman |
| 9,204,972 | B2 | 12/2015 | Weiman et al. |
| 9,204,974 | B2 | 12/2015 | Glerum et al. |
| 9,211,196 | B2 | 12/2015 | Glerum et al. |
| 9,216,095 | B2 | 12/2015 | Glerum et al. |
| 9,226,836 | B2 | 1/2016 | Glerum |
| 9,271,843 | B2 | 3/2016 | Fabian et al. |
| 9,278,008 | B2 | 3/2016 | Perloff et al. |
| 9,283,092 | B2 | 3/2016 | Siegal et al. |
| 9,295,562 | B2 | 3/2016 | Lechmann et al. |
| 9,308,099 | B2 | 4/2016 | Triplett et al. |
| 9,320,613 | B2 | 4/2016 | Dmuschewsky |
| 9,351,848 | B2 | 5/2016 | Glerum et al. |
| 9,358,125 | B2 | 6/2016 | Jimenez et al. |
| 9,358,126 | B2 | 6/2016 | Glerum et al. |
| 9,358,128 | B2 | 6/2016 | Glerum et al. |
| 9,358,129 | B2 | 6/2016 | Weiman |
| 9,370,434 | B2 | 6/2016 | Weiman |
| 9,402,739 | B2 | 8/2016 | Weiman et al. |
| 9,408,708 | B2 | 8/2016 | Greenhalgh |
| 9,414,934 | B2 | 8/2016 | Cain |
| 9,414,936 | B2 | 8/2016 | Miller et al. |
| 9,445,848 | B2 | 9/2016 | Anderson et al. |
| 9,445,918 | B1 | 9/2016 | Lin |
| 9,452,063 | B2 | 9/2016 | Glerum et al. |
| 9,456,903 | B2 | 10/2016 | Glerum et al. |
| 9,474,623 | B2 | 10/2016 | Cain |
| 9,474,625 | B2 | 10/2016 | Weiman |
| 9,480,573 | B2 | 11/2016 | Perloff et al. |
| 9,480,578 | B2 | 11/2016 | Pinto |
| 9,482,260 | B1 | 11/2016 | Krause |
| 9,486,325 | B2 | 11/2016 | Davenport et al. |
| 9,486,328 | B2 | 11/2016 | Jimenez et al. |
| 9,492,283 | B2 | 11/2016 | Glerum |
| 9,492,287 | B2 | 11/2016 | Glerum et al. |
| 9,492,288 | B2 | 11/2016 | Wagner et al. |
| 9,510,954 | B2 | 12/2016 | Glerum et al. |
| 9,522,068 | B2 | 12/2016 | Goel et al. |
| 9,539,108 | B2 | 1/2017 | Glerum et al. |
| 9,545,319 | B2 | 1/2017 | Farin |
| 9,554,918 | B2 | 1/2017 | Weiman |
| 9,561,116 | B2 | 2/2017 | Weiman et al. |
| 9,561,117 | B2 | 2/2017 | Lechmann et al. |
| 9,566,168 | B2 | 2/2017 | Glerum et al. |
| 9,579,124 | B2 | 2/2017 | Gordon et al. |
| 9,579,130 | B2 | 2/2017 | Oglaza et al. |
| 9,585,762 | B2 | 3/2017 | Suddaby et al. |
| 9,597,197 | B2 | 3/2017 | Lechmann et al. |
| 9,597,200 | B2 | 3/2017 | Glerum et al. |
| 9,610,175 | B2 | 4/2017 | Barreiro et al. |
| 9,610,176 | B1 | 4/2017 | Abdou |
| 9,615,937 | B2 | 4/2017 | Barreiro |
| 9,655,744 | B1 | 5/2017 | Pimenta |
| 9,820,788 | B2 | 11/2017 | Vrionis et al. |
| 9,888,859 | B1 | 2/2018 | Spangler et al. |
| 9,901,457 | B2 | 2/2018 | Sack et al. |
| 10,105,238 | B2 | 10/2018 | Koch et al. |
| 10,201,431 | B2 | 2/2019 | Slater et al. |
| 10,314,631 | B2 | 6/2019 | Blohm et al. |
| 10,322,009 | B2 | 6/2019 | Aghayev et al. |
| 10,327,912 | B1 | 6/2019 | Suddaby |
| 10,390,963 | B2 | 8/2019 | Olmos et al. |
| 10,500,059 | B2 | 12/2019 | Grotz |
| 10,687,876 | B2 | 6/2020 | Vrionis et al. |
| 10,792,083 | B2 | 10/2020 | Vrionis et al. |
| 10,799,367 | B2 | 10/2020 | Vrionis et al. |
| 10,898,340 | B2 | 1/2021 | Koch et al. |
| 10,945,859 | B2 | 3/2021 | Ewer et al. |
| 11,134,997 | B2 | 10/2021 | Vrionis et al. |
| 11,246,717 | B2 | 2/2022 | Aghayev et al. |
| 11,464,648 | B2 | 10/2022 | Choi et al. |
| 11,950,770 | B1 | 4/2024 | Choi et al. |
| 2001/0005796 | A1 | 6/2001 | Zdeblick et al. |
| 2001/0032017 | A1 | 10/2001 | Alfaro |
| 2002/0010511 | A1 | 1/2002 | Michelson |
| 2002/0107573 | A1 | 8/2002 | Steinberg |
| 2002/0143401 | A1 | 10/2002 | Michelson |
| 2002/0195827 | A1 | 12/2002 | Jackson et al. |
| 2003/0028251 | A1 | 2/2003 | Mathews |
| 2003/0060687 | A1 | 3/2003 | Kleeman et al. |
| 2003/0208206 | A1 | 11/2003 | Gitis et al. |
| 2003/0216748 | A1 | 11/2003 | Gitis et al. |
| 2003/0229355 | A1 | 12/2003 | Keller |
| 2003/0236472 | A1 | 12/2003 | Van Hoeck et al. |
| 2004/0002758 | A1 | 1/2004 | Landry |
| 2004/0034430 | A1 | 2/2004 | Falahee |
| 2004/0122431 | A1 | 6/2004 | Biedermann et al. |
| 2004/0210227 | A1 | 10/2004 | Trail et al. |
| 2005/0043735 | A1 | 2/2005 | Ahmad |
| 2005/0070911 | A1 | 3/2005 | Carrison et al. |
| 2005/0113917 | A1 | 5/2005 | Chae et al. |
| 2005/0143735 | A1 | 6/2005 | Kyle et al. |
| 2005/0177235 | A1 | 8/2005 | Bahnham |
| 2005/0182416 | A1 | 8/2005 | Lim |
| 2005/0197660 | A1 | 9/2005 | Haid et al. |
| 2005/0222681 | A1 | 10/2005 | Richley |
| 2005/0234555 | A1 | 10/2005 | Sutton |
| 2005/0256576 | A1 | 11/2005 | Moskowitz et al. |
| 2005/0261683 | A1 | 11/2005 | Veldhuizen et al. |
| 2005/0261695 | A1 | 11/2005 | Cragg et al. |
| 2005/0277923 | A1 | 12/2005 | Sweeney et al. |
| 2005/0278036 | A1 | 12/2005 | Leonard |
| 2006/0036322 | A1 | 2/2006 | Reiley et al. |
| 2006/0142858 | A1 | 6/2006 | Colleran |
| 2006/0149279 | A1 | 7/2006 | Mathews |
| 2006/0155297 | A1 | 7/2006 | Ainsworth et al. |
| 2006/0167547 | A1 | 7/2006 | Suddaby |
| 2006/0224241 | A1 | 10/2006 | Butler et al. |
| 2006/0287725 | A1 | 12/2006 | Miller |
| 2007/0005088 | A1 | 1/2007 | Lehuec et al. |
| 2007/0043440 | A1 | 2/2007 | William |
| 2007/0049935 | A1 | 3/2007 | Edidin |
| 2007/0067034 | A1 | 3/2007 | Chiico |
| 2007/0118222 | A1 | 5/2007 | Lang |
| 2007/0167951 | A1 | 7/2007 | Ainsworth et al. |
| 2007/0198089 | A1 | 8/2007 | Moskowitz |
| 2007/0219634 | A1 | 9/2007 | Greenhalgh |
| 2007/0260315 | A1 | 11/2007 | Foley |
| 2007/0270855 | A1 | 11/2007 | Partin |
| 2007/0276406 | A1 | 11/2007 | Mahoney et al. |
| 2007/0282449 | A1 | 12/2007 | de Villiers |
| 2008/0033440 | A1 | 2/2008 | Moskowitz |
| 2008/0045968 | A1 | 2/2008 | Yu |
| 2008/0082167 | A1 | 4/2008 | Edidin |
| 2008/0108990 | A1 | 5/2008 | Mitchell |

(56) References Cited

U.S. PATENT DOCUMENTS

| | | | |
|---|---|---|---|
| 2008/0114367 | A1 | 5/2008 | Meyer |
| 2008/0147018 | A1 | 6/2008 | Squilla et al. |
| 2008/0167657 | A1 | 7/2008 | Greenhalgh |
| 2008/0183204 | A1 | 7/2008 | Greenhal et al. |
| 2008/0195153 | A1 | 8/2008 | Altarac |
| 2008/0219604 | A1 | 9/2008 | Chen |
| 2008/0221686 | A1 | 9/2008 | Ferree |
| 2008/0243255 | A1 | 10/2008 | Butler |
| 2008/0249604 | A1 | 10/2008 | Donovan |
| 2008/0281346 | A1 | 11/2008 | Greenhalgh |
| 2008/0288072 | A1 | 11/2008 | Kohm |
| 2008/0288078 | A1 | 11/2008 | Kohm |
| 2008/0319549 | A1 | 12/2008 | Greenhalgh |
| 2009/0076607 | A1 | 3/2009 | Aalsma |
| 2009/0118771 | A1 | 5/2009 | Gonzalez-Hernandez |
| 2009/0157084 | A1 | 6/2009 | Aalsma |
| 2009/0198338 | A1 | 8/2009 | Phan |
| 2009/0222093 | A1 | 9/2009 | Liu |
| 2009/0222100 | A1 | 9/2009 | Cipoletti |
| 2009/0254129 | A1 | 10/2009 | Tipirneni et al. |
| 2009/0281551 | A1 | 11/2009 | Frey |
| 2009/0281628 | A1 | 11/2009 | Oglaza |
| 2010/0003638 | A1 | 1/2010 | Collins et al. |
| 2010/0016973 | A1 | 1/2010 | De Villiers et al. |
| 2010/0036440 | A1 | 2/2010 | Morris et al. |
| 2010/0049244 | A1 | 2/2010 | Cohen et al. |
| 2010/0082109 | A1 | 4/2010 | Greenhalgh |
| 2010/0185291 | A1 | 7/2010 | Jimenez |
| 2010/0249720 | A1 | 9/2010 | Biyani |
| 2010/0285783 | A1 | 11/2010 | Huguet et al. |
| 2010/0286783 | A1 | 11/2010 | Lechmann |
| 2010/0305705 | A1 | 12/2010 | Butler |
| 2010/0318127 | A1 | 12/2010 | Phan |
| 2010/0331883 | A1 | 12/2010 | Schmitz et al. |
| 2011/0004307 | A1 | 1/2011 | Ahr |
| 2011/0034925 | A1 | 2/2011 | Tipirneni et al. |
| 2011/0035011 | A1 | 2/2011 | Cain et al. |
| 2011/0040329 | A1 | 2/2011 | Ainsworth et al. |
| 2011/0087294 | A1 | 4/2011 | Reiley et al. |
| 2011/0106172 | A1 | 5/2011 | Wallenstein et al. |
| 2011/0125270 | A1 | 5/2011 | Paul |
| 2011/0144703 | A1 | 6/2011 | Krause et al. |
| 2011/0172774 | A1 | 7/2011 | Varela |
| 2011/0184422 | A1 | 7/2011 | Mathews |
| 2011/0224738 | A1 | 9/2011 | Sucec et al. |
| 2011/0270396 | A1 | 11/2011 | Leibowitz |
| 2011/0276141 | A1 | 11/2011 | Caratsch |
| 2011/0282378 | A1 | 11/2011 | Murphy et al. |
| 2011/0282453 | A1 | 11/2011 | Greenhalgh |
| 2011/0301712 | A1 | 12/2011 | Palmatier et al. |
| 2011/0319946 | A1 | 12/2011 | Levy et al. |
| 2011/0319997 | A1 | 12/2011 | Glerum |
| 2012/0004732 | A1 | 1/2012 | Goel |
| 2012/0053642 | A1 | 3/2012 | Lozier |
| 2012/0071977 | A1 | 3/2012 | Oglaza |
| 2012/0083887 | A1 | 4/2012 | Purcell |
| 2012/0083889 | A1 | 4/2012 | Purcell |
| 2012/0123546 | A1 | 5/2012 | Medina |
| 2012/0136442 | A1 | 5/2012 | Kleiner |
| 2012/0150241 | A1 | 6/2012 | Ragab |
| 2012/0185047 | A1 | 7/2012 | Wooley |
| 2012/0185049 | A1 | 7/2012 | Varela |
| 2012/0209386 | A1 | 8/2012 | Triplett et al. |
| 2012/0215313 | A1 | 8/2012 | Saidha |
| 2012/0215316 | A1 | 8/2012 | Mohr |
| 2012/0226357 | A1 | 9/2012 | Varela |
| 2012/0245691 | A1 | 9/2012 | Reimels |
| 2013/0006361 | A1 | 1/2013 | Glerum et al. |
| 2013/0053902 | A1 | 2/2013 | Trudeau et al. |
| 2013/0079882 | A1 | 3/2013 | Wolfe |
| 2013/0079883 | A1 | 3/2013 | Butler |
| 2013/0103103 | A1 | 4/2013 | Mire et al. |
| 2013/0103156 | A1 | 4/2013 | Packer et al. |
| 2013/0144391 | A1 | 6/2013 | Siegal |
| 2013/0158669 | A1 | 6/2013 | Sungarian |
| 2013/0190876 | A1 | 7/2013 | Dochner et al. |
| 2013/0190877 | A1 | 7/2013 | Medina |
| 2013/0211526 | A1 | 8/2013 | Alheidt et al. |
| 2013/0231747 | A1 | 9/2013 | Olmos et al. |
| 2013/0310939 | A1 | 11/2013 | Fabian |
| 2013/0325075 | A1 | 12/2013 | Jackson et al. |
| 2013/0325128 | A1 | 12/2013 | Perloff et al. |
| 2014/0012383 | A1 | 1/2014 | Triplett et al. |
| 2014/0031940 | A1 | 1/2014 | Banouskou |
| 2014/0039622 | A1 | 2/2014 | Glerum |
| 2014/0052253 | A1 | 2/2014 | Perloff et al. |
| 2014/0088714 | A1 | 3/2014 | Miller |
| 2014/0094916 | A1 | 4/2014 | Glerum et al. |
| 2014/0114312 | A1 | 4/2014 | Krause |
| 2014/0121774 | A1 | 5/2014 | Glerum et al. |
| 2014/0128977 | A1 | 5/2014 | Glerum |
| 2014/0142639 | A1 | 5/2014 | Vennard et al. |
| 2014/0163683 | A1 | 6/2014 | Seifert et al. |
| 2014/0172027 | A1 | 6/2014 | Biedermann et al. |
| 2014/0172106 | A1 | 6/2014 | To et al. |
| 2014/0188180 | A1 | 7/2014 | Biedermann et al. |
| 2014/0188224 | A1 | 7/2014 | Dmuschewsky |
| 2014/0194991 | A1 | 7/2014 | Jimenez |
| 2014/0194992 | A1 | 7/2014 | Medina |
| 2014/0249631 | A1 | 9/2014 | Weiman |
| 2014/0257484 | A1 | 9/2014 | Flower |
| 2014/0277139 | A1 | 9/2014 | Vrionis et al. |
| 2014/0277490 | A1 | 9/2014 | Perloff |
| 2014/0277497 | A1 | 9/2014 | Bennett et al. |
| 2014/0303730 | A1 | 10/2014 | Mcguire et al. |
| 2014/0324044 | A1 | 10/2014 | Haufe et al. |
| 2014/0379086 | A1 | 12/2014 | Elahinia |
| 2015/0012048 | A1 | 1/2015 | Huebner et al. |
| 2015/0012098 | A1 | 1/2015 | Eastlack |
| 2015/0018951 | A1 | 1/2015 | Loebl |
| 2015/0066145 | A1 | 3/2015 | Rogers et al. |
| 2015/0073552 | A1 | 3/2015 | To |
| 2015/0265320 | A1 | 9/2015 | Hynes et al. |
| 2015/0342586 | A1 | 12/2015 | Lim et al. |
| 2016/0030029 | A1 | 2/2016 | Mahoney et al. |
| 2016/0051373 | A1 | 2/2016 | Faulhaber |
| 2016/0128846 | A1 | 5/2016 | Voellmicke |
| 2016/0199194 | A1 | 7/2016 | Slater et al. |
| 2016/0270772 | A1 | 9/2016 | Beale et al. |
| 2016/0278791 | A1 | 9/2016 | Pellegrino et al. |
| 2016/0310190 | A1 | 10/2016 | Gonzalez et al. |
| 2016/0310291 | A1 | 10/2016 | Greenhalgh |
| 2016/0338846 | A1 | 11/2016 | Walker |
| 2017/0042695 | A1 | 2/2017 | Foley et al. |
| 2017/0056200 | A1 | 3/2017 | Koch et al. |
| 2017/0065269 | A1 | 3/2017 | Thommen et al. |
| 2017/0105845 | A1 | 4/2017 | Glerum et al. |
| 2017/0112631 | A1 | 4/2017 | Kuyler |
| 2017/0238788 | A1 | 8/2017 | Jackson |
| 2017/0258605 | A1* | 9/2017 | Blain ...................... A61F 2/441 |
| 2018/0014866 | A1 | 1/2018 | Vrionis et al. |
| 2018/0071000 | A1 | 3/2018 | Pham et al. |
| 2018/0078384 | A1 | 3/2018 | Suddaby |
| 2018/0092677 | A1 | 4/2018 | Peterson et al. |
| 2018/0092751 | A1 | 4/2018 | Vrionis et al. |
| 2018/0160923 | A1 | 6/2018 | Spangler et al. |
| 2018/0193164 | A1 | 7/2018 | Shoshtaev |
| 2018/0206897 | A1 | 7/2018 | Palmer |
| 2018/0250051 | A1 | 9/2018 | Vrionis et al. |
| 2018/0310975 | A1 | 11/2018 | Haufe et al. |
| 2019/0038435 | A1 | 2/2019 | Daffinson et al. |
| 2019/0046328 | A1 | 2/2019 | Rosenwasser et al. |
| 2019/0142407 | A1 | 5/2019 | Jung et al. |
| 2019/0142408 | A1 | 5/2019 | Jung et al. |
| 2019/0209154 | A1 | 7/2019 | Richter et al. |
| 2019/0328543 | A1* | 10/2019 | Lin .................... A61B 17/8819 |
| 2020/0015925 | A1 | 1/2020 | Scheib |
| 2020/0069435 | A1 | 3/2020 | Eastlack et al. |
| 2020/0085586 | A1* | 3/2020 | Ludwig ................... A61F 2/442 |
| 2020/0107824 | A1 | 4/2020 | Fleischer |
| 2020/0179632 | A1 | 6/2020 | Worley |
| 2020/0383675 | A1 | 12/2020 | Jung |
| 2021/0068863 | A1 | 3/2021 | Choi et al. |

(56) References Cited

U.S. PATENT DOCUMENTS

| | | | |
|---|---|---|---|
| 2021/0315710 A1 | 10/2021 | Koch et al. |
| 2021/0330472 A1 | 10/2021 | Shoshtaev |
| 2022/0175418 A1 | 6/2022 | Ebersole et al. |

FOREIGN PATENT DOCUMENTS

| | | |
|---|---|---|
| CA | 2567274 | 11/2014 |
| CN | 105636555 | 6/2016 |
| CN | 108024860 | 5/2018 |
| EP | 0260044 | 3/1988 |
| EP | 1006956 | 6/2000 |
| EP | 2693989 | 2/2014 |
| EP | 2729092 | 5/2014 |
| EP | 2793760 | 10/2014 |
| EP | 3016617 | 5/2016 |
| EP | 3038565 | 7/2016 |
| EP | 3038566 | 7/2016 |
| JP | 2004536657 | 12/2004 |
| JP | 2007521886 | 8/2007 |
| JP | 2011519673 | 7/2011 |
| JP | 6096282 | 3/2017 |
| JP | 2018525131 | 9/2018 |
| KR | 101852973 | 5/2018 |
| WO | 1998034568 | 8/1998 |
| WO | 2000025706 | 5/2000 |
| WO | 2002076335 | 10/2002 |
| WO | 2003032812 | 4/2003 |
| WO | 2005112834 | 12/2005 |
| WO | 2008070863 | 6/2008 |
| WO | 2009037509 | 3/2009 |
| WO | 2009092102 | 7/2009 |
| WO | 2010078468 | 7/2010 |
| WO | 2010105181 | 9/2010 |
| WO | 2012047712 | 4/2012 |
| WO | 2012112596 | 8/2012 |
| WO | 2012141715 | 10/2012 |
| WO | 2013052807 | 4/2013 |
| WO | 2013109346 | 7/2013 |
| WO | 2013173767 | 11/2013 |
| WO | 2014144696 | 9/2014 |
| WO | 2014151162 | 9/2014 |
| WO | 2014164625 | 10/2014 |
| WO | 2015009998 | 1/2015 |
| WO | 2015031291 | 3/2015 |
| WO | 2015063719 | 5/2015 |
| WO | 2017015165 | 1/2017 |
| WO | 2017027277 | 2/2017 |
| WO | 2017035155 | 3/2017 |
| WO | 2017051416 | 3/2017 |
| WO | 2021050577 | 3/2021 |
| WO | 2021241890 | 12/2021 |

OTHER PUBLICATIONS

Eum, Jin Hwa et al. "Percutaneous biportal endoscopic decompression for lumbar spinal stenosis: a technical note and preliminary clinical results." J Neurosurg Spine 24:602-607, Apr. 2016; published online Jan. 1, 2016, 7 pages.

Innovasive Inc. "INNOVASIVE DualX LLIP expanding IBFD Product Information and Instructions for Use." May 2018, 2 pages.

International Bureau, Written Opinion, PCT Patent Application PCT/US2016/048222 filed Aug. 23, 2016; mailed Mar. 2, 2017, 8 pages.

ISA, International Search Report and Written Opinion, PCT Patent Application PCT/US2020/049982, mailed Jan. 26, 2021, 21 pages.

Kim, Jin-Sung et al., "Endoscope-assisted oblique lumbar interbody fusion for the treatment of cauda equina syndrome: a technical note." Eur Spine J (2017) 26:397-403, 7 pages.

International search Report and Written Opinion for PCT/US2021/063881 mailed May 4, 2022, 32 pages.

European Search Report for Application No. Patent No. 21907844.1-1122 / 4262636 PCT/US2021/063881 mailed Oct. 14, 2024, 9 pages.

International Preliminary Report on Patentability and Written Opinion for Application No. PCT/US2022/019706 mailed Sep. 21, 2023, 8 pages.

International Search Report and Written Opinion for Application No. PCT/US2022/019706 mailed Jun. 20, 2022, 13 pages.

European Search Report for Application No. 20863847.8 received Sep. 18, 2023, 7 pages.

Japanese Office Action for Application No. 2022-541192 mailed Mar. 11, 2024, 10 pages with English translation.

First Examination Report for Application No. 20863847.8 mailed Sep. 12, 2024, 4 pages.

First Office Action for Chinese Application No. 202080078070.2 mailed Sep. 20, 2024, 40 pages with English translation.

International Preliminary Report on Patentability, PCT Patent Application No. PCT/US2020/049982 mailed Mar. 17, 2022, 17 pages.

Final Office Action mailed Jul. 20, 2020 in U.S. Appl. No. 16/043,116, 6 pages.

Non-Final Office Action mailed Dec. 19, 2019 in U.S. Appl. No. 16/043,116, 8 pages.

Non-Final Office Action mailed Jun. 12, 2018 in U.S. Appl. No. 15/244,446, 9 pages.

Notice of Allowance mailed Jul. 13, 2018 in U.S. Appl. No. 15/244,446, 5 pages.

Notice of Allowance mailed Sep. 22, 2020 in U.S. Appl. No. 16/043,116, 5 pages.

International Search Report and Written Opinion, PCT Patent Application PCT/US2024/018567, mailed Aug. 8, 2024, 26 pages.

Office Action of U.S. Appl. No. 16/443,302, mailed Feb. 3, 2021, 34 pages.

Office Action issued for U.S. Appl. No. 15/970,212, dated Sep. 24, 2020, 16 pages.

Final Office Action issued in U.S. Appl. No. 15/718,786, mailed Mar. 19, 2020, 17 pages.

Notice of Allowance issued for U.S. Appl. No. 15/970,212, dated Jun. 3, 2021, 6 pages.

International Preliminary Report on Patentability and Written Opinion, dated Jun. 21, 2016, received in connection with International Patent Application No. PCT/US2014/070899, 1 page.

International Search Report and Written Opinion, dated May 14, 2015, received in connection with International Patent Application No. PCT/US2014/070899, 15 pages.

International Preliminary Report on Patentability and Written Opinion, dated Apr. 8, 2014, received in connection with International Patent Application No. PCT/US2012/0589681, 1 page.

International Search Report and Written Opinion for PCT/US2012/058968 mailed Mar. 28, 2013, 17 pages.

International Preliminary Report on Patentability issued in PCT/US2015/043109, mailed Feb. 16, 2017, 2 pages.

International Search Report and Written Opinion for issued in PCT/US2015/043109, mailed Nov. 2, 2015, 8 pages.

Zimmer® Herbert™ Cannulated Bone Screw, Webpage, http://www.zimmerbiomet.com/content/dam/zimmer-biomet/medicalprofessionals/000-surgical-techniques/trauma/zimmer-herbert-cannulated-bone-screw.pdf, dated Jul. 27, 2015, accessed Jan. 2, 2018, 7 pages.

* cited by examiner

DRIVE INSTRUMENTS WITH RETENTION MECHANISMS, MEDICAL IMPLANTS, AND RELATED TECHNOLOGIES

CROSS-REFERENCE TO RELATED APPLICATION

This application is a continuation of International Application No. PCT/US2022/019706, filed on Mar. 10, 2022, which claims the benefit of U.S. Provisional Patent Application No. 63/159,327, filed on Mar. 10, 2021. The above-identified applications are all incorporated herein by reference in their entireties

TECHNICAL FIELD

The present technology relates generally to drive instruments with retention mechanisms and, more particularly, to systems, devices, and methods for implanting medical devices.

BACKGROUND

Implants are often positioned at implantation sites within patients to treat various medical conditions, such as nerve compression and/or damaged or displaced spinal discs and/or vertebral bodies due to trauma, disease, degenerative defects, or wear over an extended period of time. One result of nerve compression and/or displacement or damage to a spinal disc or vertebral body may be chronic back pain. One procedure for treating the spine may involve partial or complete removal of tissue (e.g., an intervertebral disc, tissue contributing to stenosis, etc.) from a target implantation site, and implanting an implantable device along the spine to, for example, replace biological structures or support organs and tissues, reduce nerve compression, help maintain height of the spine, and/or restore stability to the spine. Such implantable device can include spinal fusion devices (e.g., pedicle screw and rods), which can fuse together one or more segments of the spine; interspinous spacers, which can hold apart adjacent vertebrae to help eliminate or reduce nerve compression; and/or intervertebral spacers, which may provide a lordotic correction to the curvature of the spine. However, it may be difficult to position these and other devices at the target implantation site and/or manipulate these devices while they are positioned at the target implantation site.

DETAILED DESCRIPTION

Figure 1:
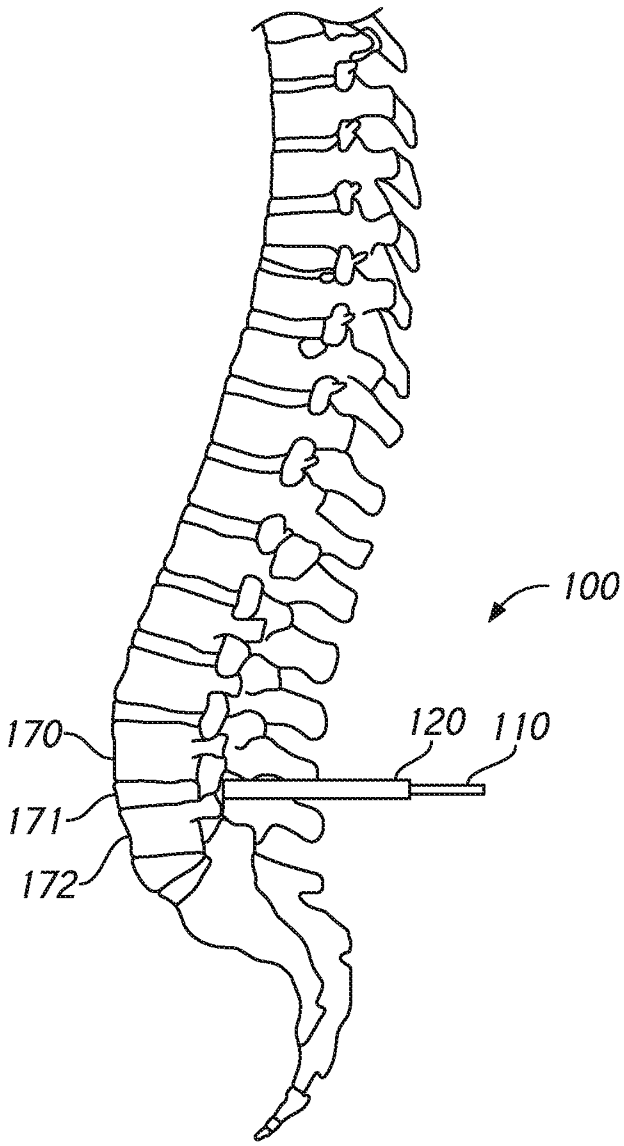
FIG. 1 is a side view of a spinal surgical system in accordance with embodiments of the present technology.

The present technology generally relates to drive instruments with retention mechanisms and, more particularly, to systems, devices, and methods for implanting medical devices. Certain details are set forth in the following description and in FIGS. 1-19 to provide a thorough understanding of such embodiments of the present technology. Other details describing well-known structures and systems often associated with, for example, surgical procedures are not set forth in the following description to avoid unnecessarily obscuring the description of various embodiments of the present technology.

In some embodiments, a drive instrument for use with implantable devices includes a retention mechanism having or more grippers or springs (e.g., a split leaf spring, cantilever spring, multi-prong spring) inside of a screwdriver or screwdriving body. The screwdriving body has a female socket for receiving a male driving head of a screw. The retention mechanism can be inserted at least partially into a screw pocket of the male driving head. The retention mechanism can couple/attach to the male driving head of the screw via a retention feature (e.g., an undercut pocket, a groove/channel, etc.) to captively hold the screw relative to the drive instrument for transport, insertion through access instruments, tightening, etc. The screw can be insertable at least partially within an implantable device, such as an intervertebral device for treating a patient's spine. In at least some embodiments, for example, the intervertebral device can be implanted in an intervertebral space to at least partially support the patient's spine. The drive instrument can detachably attach to screws or other drive elements before, during, or after insertion into patient. The retention mechanism can release the screw after transport, insertion, achieving desired tightening, and/or positioning of the implantable device at a target implant location.

In some embodiments, a system can include an implantable device and a drive instrument. The drive instrument can include a retention mechanism configured to selectively hold and release (e.g., detachably couple, releasably couple, etc.) the device. The retention mechanism can include a socket configured to receive a drive portion of the implantable device to rotationally fix the drive instrument to the implantable device. The retention mechanism can include a spring element biased outwardly to releasably hold the drive portion in the socket when the spring element extends into the drive portion. The drive portion can be a head of a screw or other drive feature. The implantable device can be an expandable device (e.g., intervertebral cage, expandable spacer, etc.), a non-expandable device, a screw (e.g., pedicle screw, bone screw, etc.), a fixation device, or the like.

In several of the embodiments described below, a system for treating a spine of a subject can include an intervertebral spacer configured to be implanted between a first vertebra and a second vertebra of the subject's spine. The intervertebral spacer can be movable between a first (e.g., unexpanded) configuration and a second (e.g., expanded) configuration. The system can further include a locking member having a (i) threaded distal region configured to threadably engage the intervertebral spacer and (ii) a proximal drive head opposite the threaded distal region, and a drive instrument assembly configured to rotate the locking member to move the intervertebral spacer from the first (unexpanded) configuration to the second (expanded) configuration. The drive instrument assembly can include a retention mechanism detachably couplable to the locking member. The retention mechanism can include a socket configured to receive the locking member's drive head to rotationally fix the drive instrument relative to the locking member, and a spring element biased outwardly to releasably hold the drive head in the socket when the spring element is received within the drive head.

In some embodiments, a system can include a drive instrument assembly configured to detachably couple to a rotatable element, such as a screw (e.g., a drive screw, a locking screw, etc.). The screw can be integrated into or part of another device, such as an expandable implant. In some procedures, the screw can be inserted within or coupled to another component while the screw is inside the patient. The drive instrument assembly can include a screwdriver configured to apply a desired force (e.g., torque, axial force, etc.) to the screw, for example, to cause the implant to expand or otherwise transition between configurations. To remove the drive instrument assembly from the patient, the user can pull the screwdriver proximally to overcome a biasing retention force coupling the screw to the screwdriver. Before, during, and/or after the drive instrument assembly is removed from the patient, the implant can engage the patient's tissue (e.g., spinal tissue, such as one or more of the patient's vertebra) to keep the implant positioned at the implantation site.

In some embodiments, the screwdriver can include a retention mechanism having a female feature that receives a male feature of the screw. For example, a head of the screw can be inserted into a female socket. The retention mechanism can include one or more grippers that automatically grip the head when the head is inserted into the socket. The grippers can correspond to and/or be insertable at least partially within a corresponding recess or chamber of the male feature of the screw, such that the grippers can provide a desired retention force to releasably couple the screw to the screwdriver. This can allow a user to use the drive instrument to carry and manipulate the retained screw. In some procedures, the drive instrument assembly holds the screw through an access port, an access instrument (e.g., a cannula, a trocar, etc.), or the like, configured to provide access to a target implant location within a patient. The drive instrument assembly can then be used to rotate the screw inside the patient to, for example, manipulate or adjust an implantable device. In some procedures, the drive instrument assembly can be coupled to the head of a screw already positioned in the patient.

In some embodiments, a screwdriver includes a drive shaft and a retention mechanism connected to the drive shaft. The retention mechanism can include a socket head and a gripper extending at least partially through a passageway of the socket head. The gripper can be inserted into a passageway of a drive head. In some embodiments, the drive head can be inserted into the socket such that the gripper is positioned within the passageway. The gripper can include one or more biasing elements which can apply sufficient force to hold the drive head in the socket. In some embodiments, the gripper can be inserted within the socket regardless of the relative angular/radial orientations of the gripper and the drive head, respectively. This can allow the drive head to be inserted into the socket at any suitable angular position. The gripper can include one or more cantilevered springs, prongs, compression springs, or combinations thereof. The configuration of the gripper can be selected based on the desired retention forces and/or the forces needed to separate the screwdriver from the drive head. The gripper can help keep at least a portion of the drive head positioned within the socket during use. In some embodiments, the gripper can keep the drive head translationally fixed with respect to the socket when the socket rotates the drive head.

Embodiments of the present technology will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

FIG. 1 is a side view of a spinal surgical system 100 ("system 100") positioned along a human subject's spine in accordance with embodiments of the present technology.

The system 100 can include an instrument 110 and a cannula 120. A series of tools and/or other devices, including the instrument 110, can be delivered through the cannula 120 to perform a surgical procedure. In some procedures, the instrument 110 can be used to prepare an implantation site by, for example, moving organs or tissue (e.g., moving nerve tissue), removing tissue (e.g., removing the intervertebral disc 171, removing tissue contributing to stenosis, etc.), preparing vertebral bodies (e.g., roughening or shaping vertebral endplates), or the like. In some embodiments, the instrument 110 can be removed and a distraction instrument (not shown) can be delivered through the cannula 120. The distraction instrument can distract adjacent vertebrae 170, 172, thereby enlarging the intervertebral space. In some embodiments, an intervertebral spacer can be delivered through the cannula 120 and into the enlarged intervertebral space. In some embodiments, the instrument 110 can be configured to deliver the intervertebral spacer through the cannula 120. In some embodiments, the intervertebral spacer can be expanded to contact one or more adjacent vertebral endplates (e.g., a lower endplate of the upper vertebra 170 and/or an upper endplate of the lower vertebra 172). The instrument 110 can be further configured to drive the expansion of the expandable intervertebral spacer. In at least some embodiments, for example, the instrument 110 can be or include one or more of the instruments, drive instrument assemblies, and/or other devices described in detail below with reference to FIGS. 2A-18.

Figure 2A:
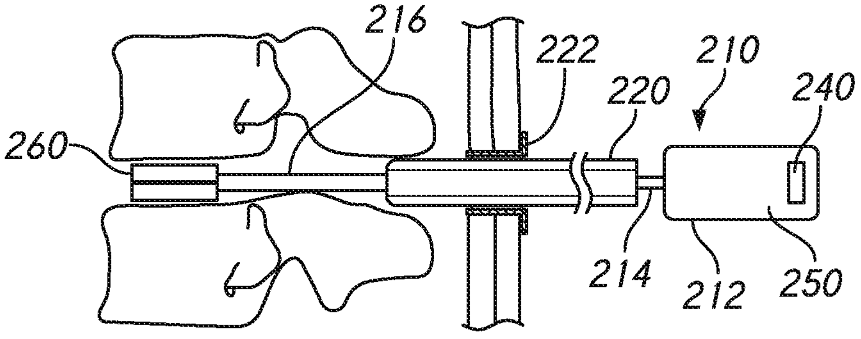
FIG. 2A is a side view of an intervertebral spacer in an unexpanded configuration and positioned in an intervertebral space, in accordance with embodiments of the present technology.
Figure 2B:
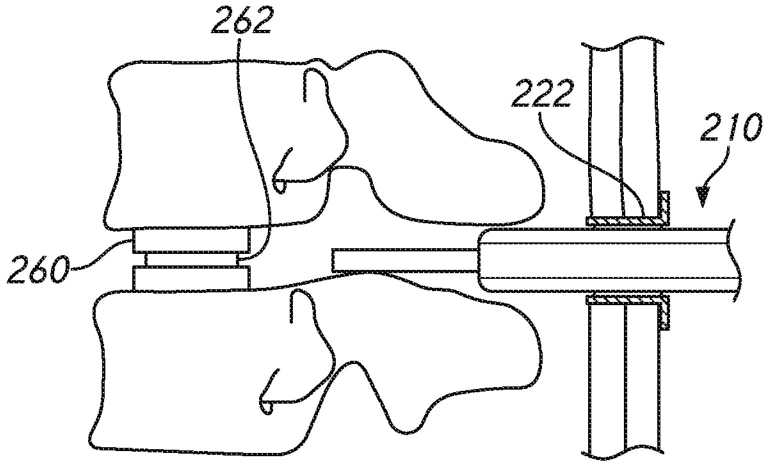
FIG. 2B is a side view of the intervertebral spacer of FIG. 2A in an expanded configuration.

FIGS. 2A and 2B are side views of an intervertebral spacer 260 positioned in an intervertebral space in accordance with embodiments of the present technology. In FIG. 2A the intervertebral spacer 260 is in a first (e.g., unexpanded configuration) and releasably coupled to an instrument 210, which can include at least some aspects that are generally similar or identical in structure and/or function to the instrument 110 of FIG. 1. The intervertebral spacer 260 and instrument 210 can be delivered through a port 222, with or without the use of a cannula 220, which can include at least some aspects that are generally similar or identical in structure and/or function to the cannula 120 of FIG. 1.

The instrument 210 can include a handle assembly 212, an elongated body 214, and a drive assembly 216. The handle assembly 212 can include a grip 250 and one or more control elements 240 operable to control operation of the intervertebral spacer 260 and control decoupling from the intervertebral spacer 260. For example, the grip 250 and/or one or more control elements 240 can apply a proximal force to decouple the intervertebral spacer 260 from the drive assembly 216. In some embodiments, the control elements 240 can include one or more dials, levers, triggers, or other movable elements. The drive assembly 216 can be connected to the grip 250 by the elongated body 214. The elongated body 214 and/or the grip 250 can include one or more rods, shafts, or other elements used to manipulate the drive assembly 216 to operate the intervertebral spacer 260. In some embodiments, a locking member (e.g., locking member 500 of FIG. 4) is coupled to a proximal end of the drive assembly 216 and operably engaged with the intervertebral spacer 260. In some embodiments, the locking member can be rotated to gradually and controllably transition the intervertebral spacer 260 between the first and second configurations. In other embodiments, the drive assembly 216 can both couple the intervertebral spacer 260 to the instrument 210 and drive (e.g., reconfigure, operate, expand, collapse, etc.) the intervertebral spacer 260 between the first and second configurations. The features, configuration, and/or functionality of the drive assembly 216 can be selected based on and/or to correspond with the configuration of the intervertebral spacer 260.

In FIG. 2B the intervertebral spacer 260 is in an expanded configuration and the delivery instrument 210 has been separated from a connection feature or connection interface 262 ("connection feature 262") of the intervertebral spacer 260. The connection feature 262 can be releasably coupled to the drive assembly 216, and can be operable to expand the intervertebral spacer 260 from an unexpanded to an expanded configuration. In some embodiments, the connection feature 262 can include a locking member releasably coupled to a proximal end of the drive assembly 216 and insertable into the intervertebral spacer 260. The locking member and/or the connection feature 262 can maintain the intervertebral spacer 260 in the expanded configuration. To reposition the intervertebral spacer 260, the instrument 210 can be reconnected to the intervertebral spacer 260 and operated to unlock and collapse the intervertebral spacer 260. The delivery instrument 210 can be used to move the collapsed intervertebral spacer 260.

The delivery instrument 210 can include one or more distal connection elements or features for detachably coupling the delivery instrument 210 to the intervertebral spacer 260 and/or the connection feature 262. These connection elements can include a polygonal connection (e.g., a hexagonal protrusion) received by a complementary polygonal recess or feature of the intervertebral spacer 260. In some embodiments, the connection feature 262 can be insertable into the intervertebral spacer 260, releasably attached to the delivery instrument 210, and can be released from the delivery instrument 210 when inserted into the intervertebral spacer 260. The delivery instrument 210 can be configured to expand one or more spacers (e.g., intervertebral spacers, interspinous spacers, etc.) at different levels along the spine. Example delivery instruments and locking elements for intervertebral spacers are discussed in detail below with reference to FIGS. 3A-19. Example intervertebral spacers are discussed in detail below with reference to FIGS. 3A-3D, as well as in U.S. Pat. Nos. 10,105,238 and 10,201,431, which are hereby incorporated by reference in their entireties.

Figure 3A:
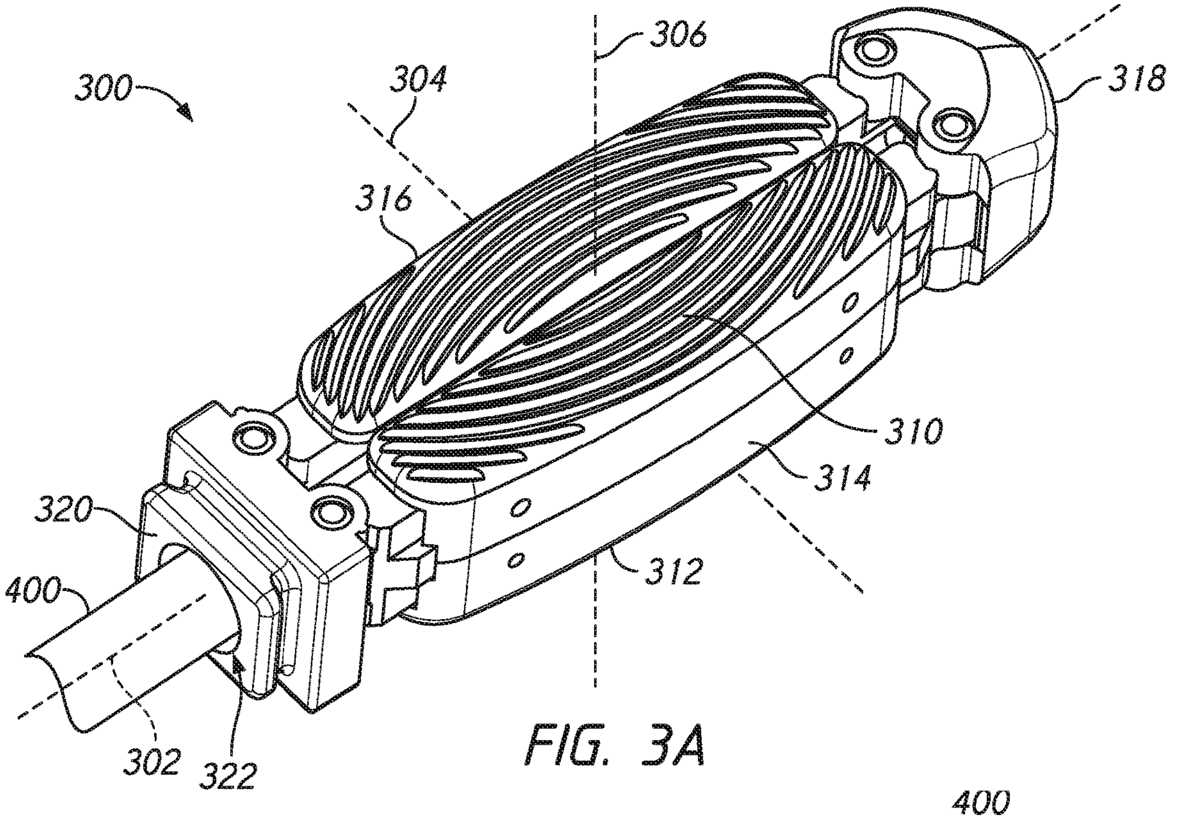
FIG. 3A is an isometric view of an intervertebral spacer in an unexpanded configuration in accordance with embodiments of the present technology.
Figure 3B:
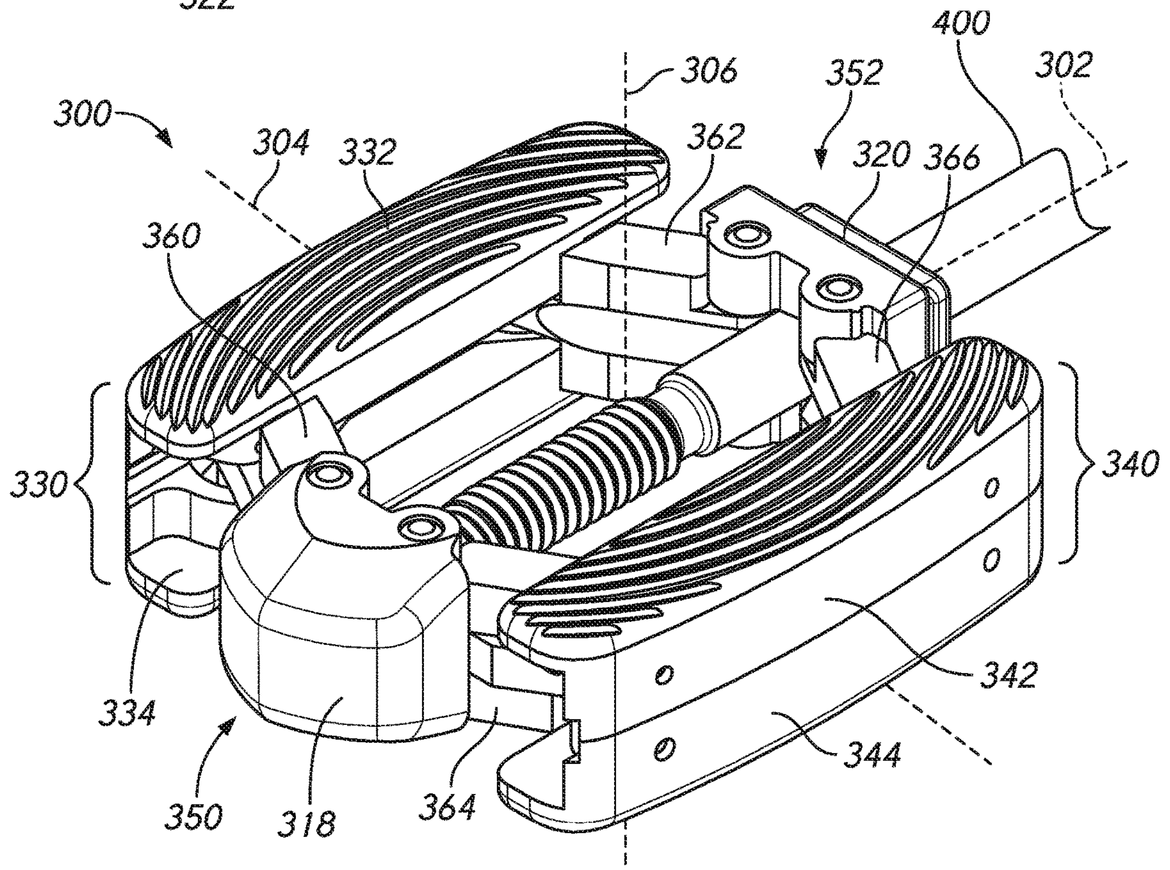
FIG. 3B is an isometric view of the intervertebral spacer of FIG. 3A in a horizontally expanded configuration in accordance with embodiments of the present technology.
Figure 3C:
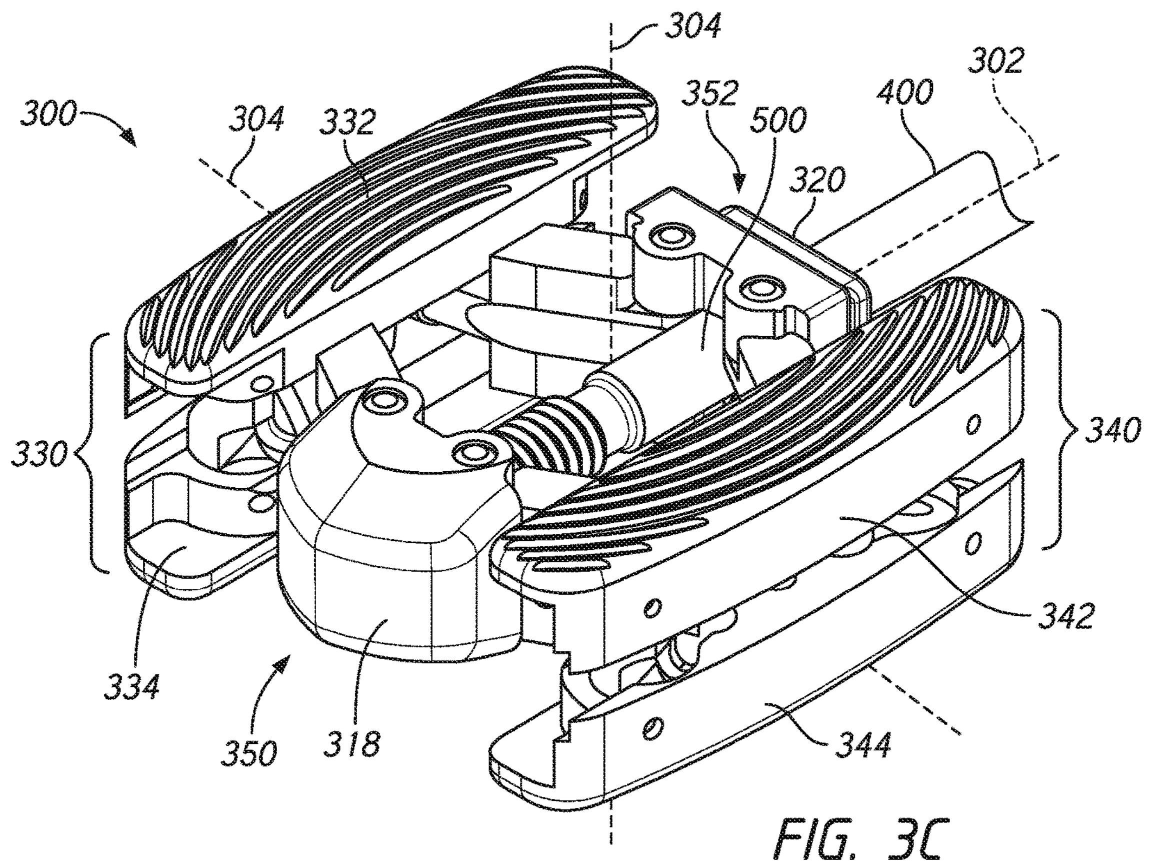
FIGS. 3C and 3D are isometric views of the intervertebral spacer of FIG. 3A in a horizontally and vertically expanded configuration in accordance with embodiments of the present technology.
Figure 3D:
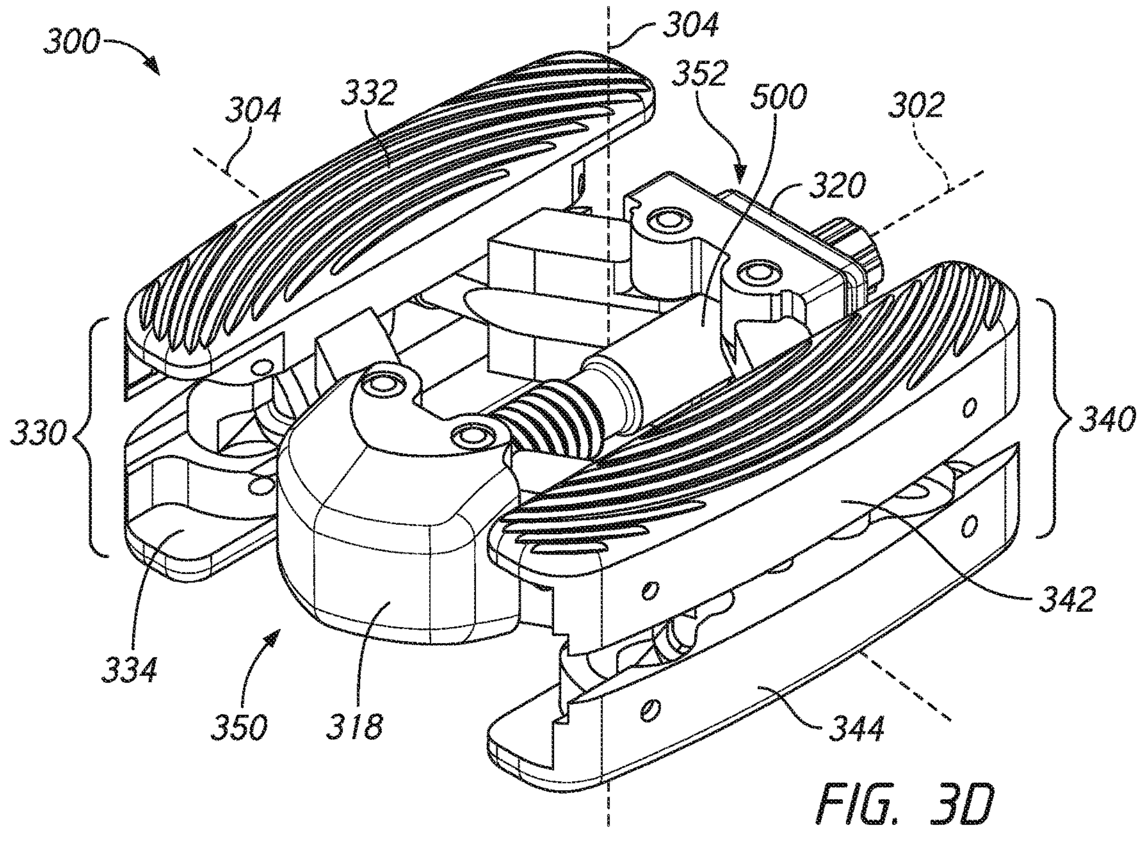

FIGS. 3A-3D are isometric views of an embodiment of an intervertebral spacer 300 ("spacer 300") at various stages of horizontal and/or vertical expansion, in accordance with embodiments of the present technology. The spacer 300 may also be referred to as a device, cage, insert, implant, or the like. FIG. 3A illustrates the spacer 300 in an unexpanded (e.g., compact, compressed, collapsed, delivery, etc.) configuration. The spacer 300 includes a lengthwise spacer axis 302, and may be expandable in a first direction along a first axis 304, which may be a horizontal or lateral expansion axis, to a horizontally expanded configuration, as shown in FIG. 3B. The spacer 300 may be further expanded in a second direction along a second axis 306, which may be a vertical expansion axis, to a horizontally and vertically expanded configuration, as shown in FIGS. 3C and 3D. Axes 304, 306 may be perpendicular to each other and/or to the spacer axis 302.

Referring to FIGS. 3A-3C, when implanted between two vertebral bodies in a portion of a spine (e.g., as illustrated in FIGS. 2A and 2B), the spacer 300 is expandable horizontally, or substantially anterior-posteriorly, along the first axis 304, and vertically, or cephalad-caudally, along the second axis 306. A single axial force acting along the spacer axis 302 may provide the expansion force for both the horizontal and vertical expansion. The spacer 300 may be bilaterally symmetrical with respect to a vertical plane extending along spacer axis 302, and may be bilaterally symmetrical with respect to a horizontal plane extending along spacer axis 302. In an alternate embodiment, the spacer may be expandable medial-laterally. In other embodiments, the spacer may be asymmetrically expandable anterior-posteriorly, cephalad-caudally, and/or medial-laterally. It is understood that any one of the spacers disclosed within may also be implanted non-parallel to the sagittal plane of the vertebral bodies, in which instance horizontal spacer expansion may not be strictly anterior-posterior or medial-lateral.

Referring to FIG. 3A, the spacer 300 includes an upper surface 310 and a lower surface 312 separated by a first side 314 and a second side 316. The spacer 300 can further include a first end body 318 and a second end body 320 separated by the upper and lower surface 310, 312 and first and second sides 314, 316. The second end 320 can include a port 322 via which the space 300 can be releasably coupled to a drive instrument assembly 400 (which can also be referred to as a delivery instrument, a delivery instrument assembly, an instrument, an insertion tool, and the like). The drive instrument assembly 400 can include at least some aspects that are generally similar or identical in structure and/or function to the instrument 110 of FIG. 1, the instrument 210 of FIGS. 2A and 2B, and/or the drive assembly 216 of FIGS. 2A and 2B. The drive instrument assembly 400 can be configured to drive the horizontal and/or vertical expansion of the spacer 300 such that the drive instrument assembly 400 can be used to deliver, position, and/or expand the spacer 300, for example, when the spacer 300 is positioned within an intervertebral space. The drive instrument assembly 400 can be configured to detachably hold the spacer 300.

Referring to FIG. 3B, the intervertebral spacer 300 comprises a set of bodies pivotably linked together, allowing the bodies to articulate relative to one another. A first support member 330 includes a first upper body 332 and a first lower body 334. A second support member 340 includes a second upper body 342 and a second lower body 344. The first end body 318 is pivotably linked to the first and second support members 330, 340 toward a first end 350 of the spacer 300, and the second end body 320 is pivotably linked to the first and second support members 330, 340 toward a second end 352 of the spacer 300. The upper and lower bodies may be mirror images of one another, as may the first and second support members. In an alternate embodiment, the first and second support members 330 and 340 may be of differing proportions and/or configuration in order to provide asymmetric expansion.

After or during insertion between the vertebral bodies, the drive instrument assembly 400 may be manipulated to urge horizontal expansion of the spacer 300. For example, drive instrument assembly 400 can be detachably coupled to a locking member (such as locking member 500 of FIG. 4), and the locking member may be rotated or ratcheted to provide an axial force along axis 302 to urge first end body 318 and second end body 320 toward one another, decreasing the distance between them. The axial force can push the first and second support members 330, 340 outward and away from one another along axis 304, from the unexpanded configuration seen in FIG. 3A into the horizontally expanded configuration seen in FIG. 3B. During this horizontal expansion, links 360, 362, 364, 366 pivot outward, or laterally relative to axis 302.

Referring to FIGS. 3B-3C, further axial force along axis 302, which may be attained by further rotation of the drive instrument assembly 400 and/or the locking member 500, can push the upper 332, 342 and lower 334, 344 bodies away from one another along axis 306, from the vertically unexpanded configuration seen in FIGS. 2A and 3B into the vertically expanded configuration seen in FIGS. 2B, 3C, and 3D.

Referring to FIG. 3D, after attaining the desired expansion of the spacer 300, the drive instrument assembly 400 (not shown) can be decoupled from the locking member 500. The locking member 500 can remain in the spacer 300 and can be configured to lock the spacer 300 in a horizontally and/or vertically expanded configuration.

In some embodiments of the present technology, the spacer could be expanded on only one side; for example, support member 330 could be horizontally and/or vertically expanded while support member 340 remains in its collapsed position, or vice versa. In another embodiment, a non-expanding support member such as 340 could be solid. This type of asymmetrical expansion could provide a lordotic or kyphotic correction.

In a method of use, a patient may be prepared by performance of a discectomy between two target vertebral bodies at a target implant location. A lateral or anterior approach may be used. The vertebral bodies may be distracted, and the spacer 300 may be mounted on and/or otherwise coupled to a suitable insertion instrument, such as the delivery instrument 400 or any other suitable delivery instrument, and inserted into the prepared space between the two target vertebral bodies. In one example, the spacer 300 is releasably coupled to the drive instrument assembly 400. The spacer 300 may be inserted within a patient with first end 350 leading. If necessary, force may be applied to the instrument 400 and the spacer 300 to facilitate insertion; the second end body 320 can be configured to withstand and/or transmit such insertion forces. Before and/or during insertion, the spacer 300 can be in the collapsed/unexpanded configuration, such as shown in FIGS. 2A and 3A. The expansion of the spacer 300 can begin when the spacer 300 is partially or fully positioned within the intervertebral space.

Figure 4:
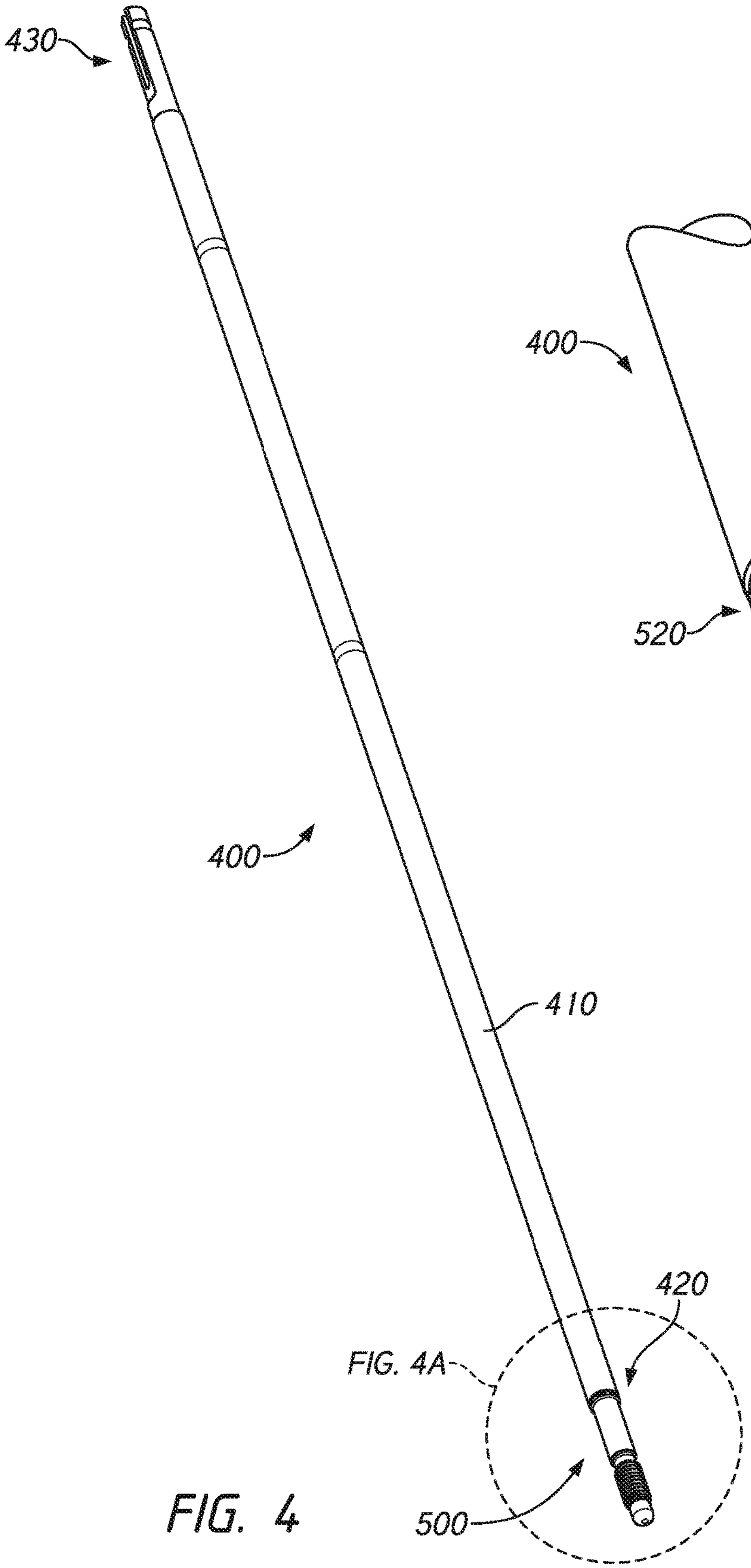
FIGS. 4 and 4A are isometric views of a drive instrument assembly and a locking member in accordance with embodiments of the present technology.
Figure 4A:
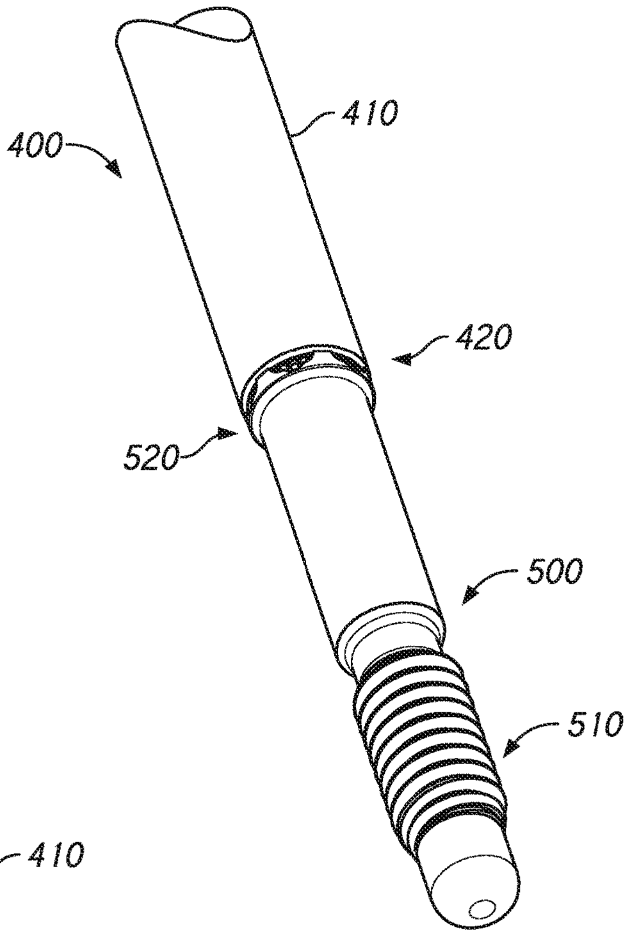

FIGS. 4 and 4A are isometric views of a drive instrument assembly 400 releasably coupled to a locking member 500 in accordance with an embodiment of the present technology. Referring to FIG. 4, The drive instrument assembly 400 can include an elongate drive shaft 410 having a distal retention mechanism 420 and a proximal connecting region 430. The retention mechanism 420 is configured to selectively (e.g., releasably, detachably, etc.) hold the locking member 500. After rotating the locking member 500 to deploy the implant, a gripping force of the retention mechanism 420 can be overcome (e.g., by pulling the drive instrument assembly 400 away from the locking member 500) to separate the retention mechanism 420 from the locking member 500 and the deployed implant.

FIG. 4A shows the locking member 500 can include a distal threaded region 510 configured to threadably engage an intervertebral spacer. For example, the threaded region 510 can threadably engage the first and/or second end body 318, 320 of the spacer 300 of FIGS. 3A-D to move the spacer 300 from the unexpanded configuration of FIG. 3A to the horizontally expanded configuration of FIG. 3B and/or to the vertically expanded configuration of FIG. 3C. With continued reference to FIG. 4A, the locking member 500 further includes a drive head 520 that can be at least partially received by the retention mechanism 420.

Figure 5:
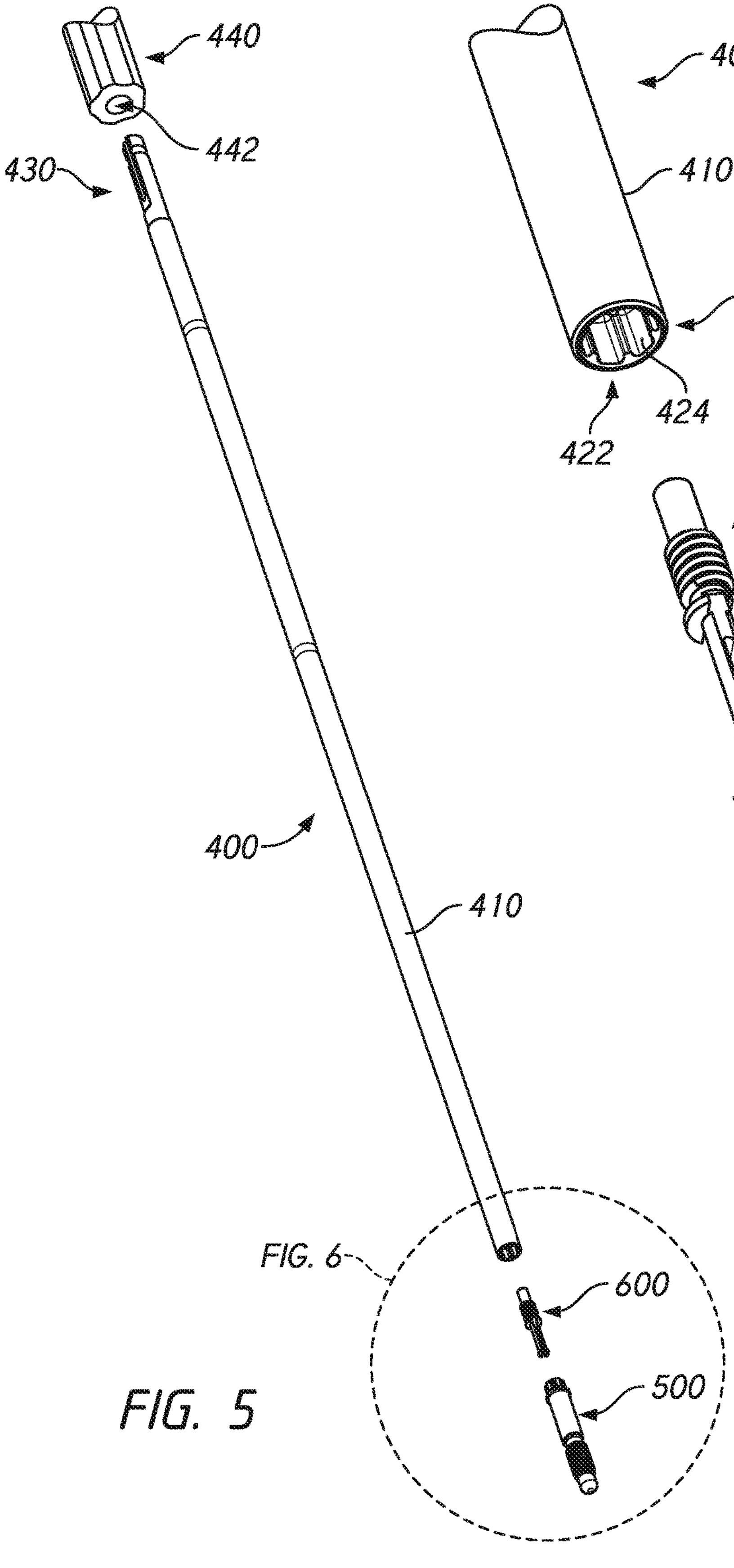
FIG. 5 is an exploded isometric view of the drive instrument assembly and the locking member of FIG. 4 in accordance with embodiments of the present technology.
Figure 6:
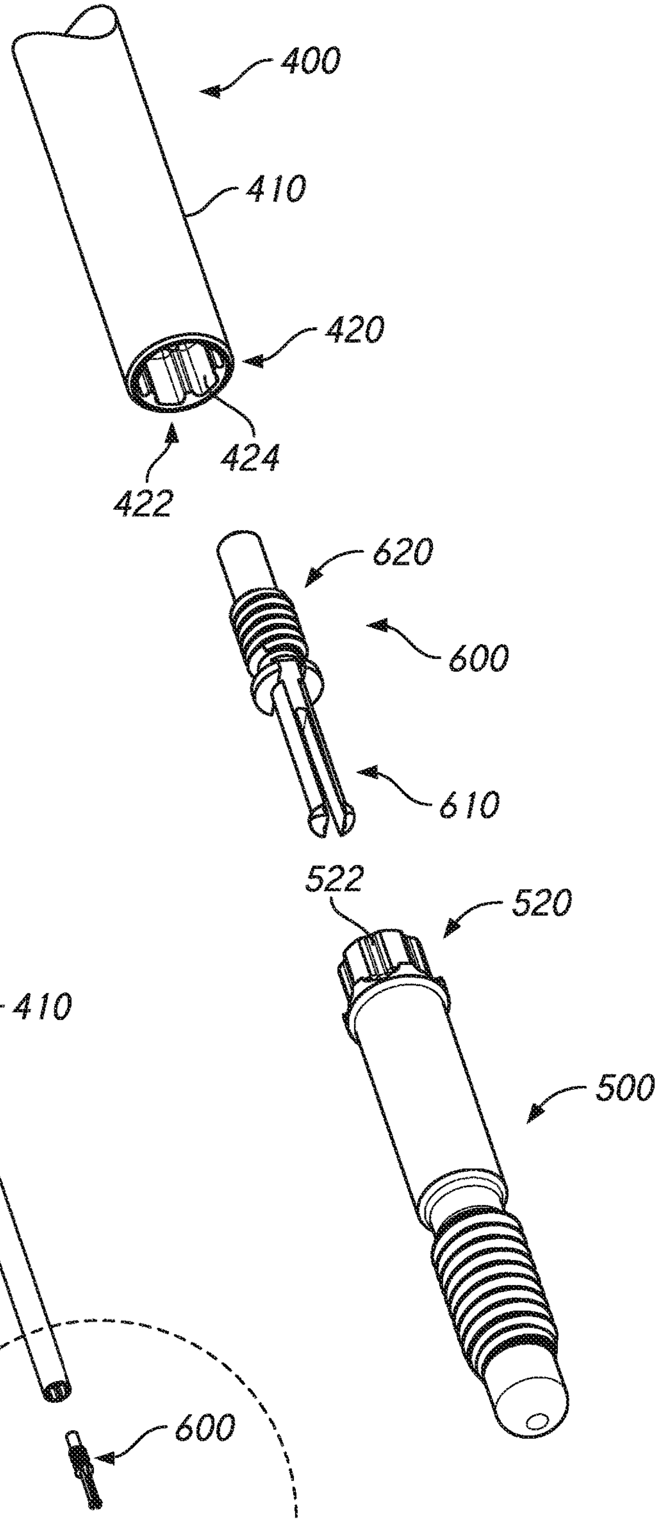
FIG. 6 is an exploded isometric view of a retention mechanism of the drive instrument assembly and the locking member of FIG. 5 in accordance with embodiments of the present technology.

FIGS. 5 and 6 are exploded isometric views of the drive instrument assembly 400 in accordance with embodiments of the present technology. Referring first to FIG. 5, the drive instrument assembly 400 can include a proximal grip or handle 440. The handle 440 can be configured for a user's hand and can be used to manipulate the drive instrument assembly 400 and/or the locking member 500. In some embodiments, the handle 440 can include a port 442 configured to detachably couple to the connecting region 430. In other embodiments, the handle 440 and the drive shaft 410 can be a one-piece component.

Referring to FIG. 6, the locking member can include a drive head 520 configured to be releasably received by the retention mechanism 420 of the drive instrument assembly 400. In the illustrated embodiment, for example, the retention mechanism 420 includes a socket 422 having a plurality of interior grooves 424, and the drive head 520 includes a plurality of exterior grooves 522 configured to slidably and/or matingly receive the interior grooves 424 of the retention mechanism 420. The interior grooves 424 (e.g., of socket 422) can correspond to the exterior grooves 522 (e.g., of drive head 520) so that the locking member 500 can be rotationally fixed to the drive shaft 410 when the drive head 520 is inserted into the socket 422. This can allow the drive shaft 410 and/or drive instrument assembly 400 to rotate the locking member 500 to expand, collapse, and/or otherwise adjust the configuration of an intervertebral spacer, such as the spacer 300 described in detail previously with reference to FIGS. 3A-3D.

The drive instrument assembly 400 can further include a connecting member 600 carried by the socket 422. The connecting member 600 can be configured to couple the locking member 500 to the drive instrument assembly 400. In some embodiments, the connecting member 600 can be part of the retention mechanism 420 of the drive instrument assembly 400, and can include a biasing or spring element 610 configured to releasably couple the locking member 500 to the drive instrument assembly 400, for example, when the drive head 520 is inserted within the socket 422. Additionally, or alternatively, the connecting member 600 can include a threaded region 620 configured to be threadably received within the socket 422.

Figure 7:
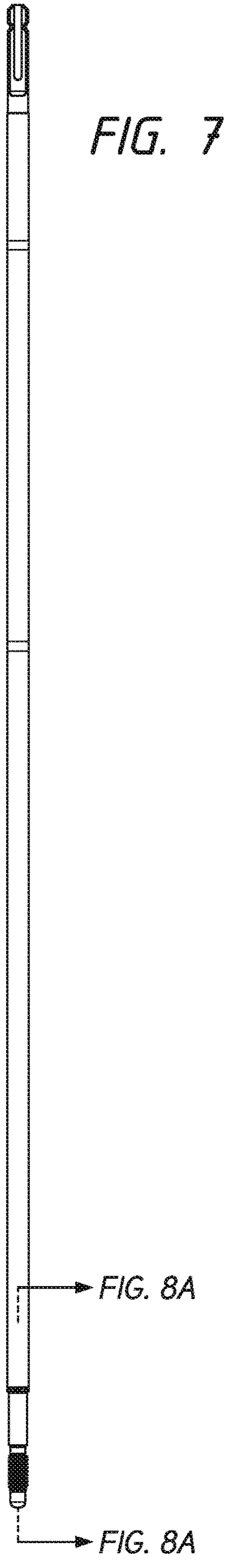
FIG. 7 is a side view of the drive instrument assembly of FIG. 4 and the locking member of FIG. 4 in accordance with embodiments of the present technology.
Figure 8A:
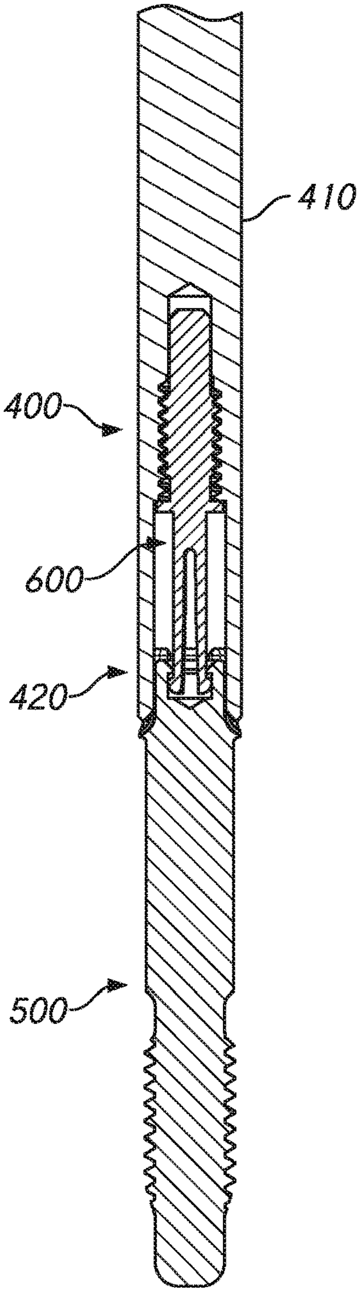
FIG. 8A is a cross-sectional view of the drive instrument assembly and locking member along line 8A-8A of FIG. 7 in accordance with embodiments of the present technology.
Figure 8B:
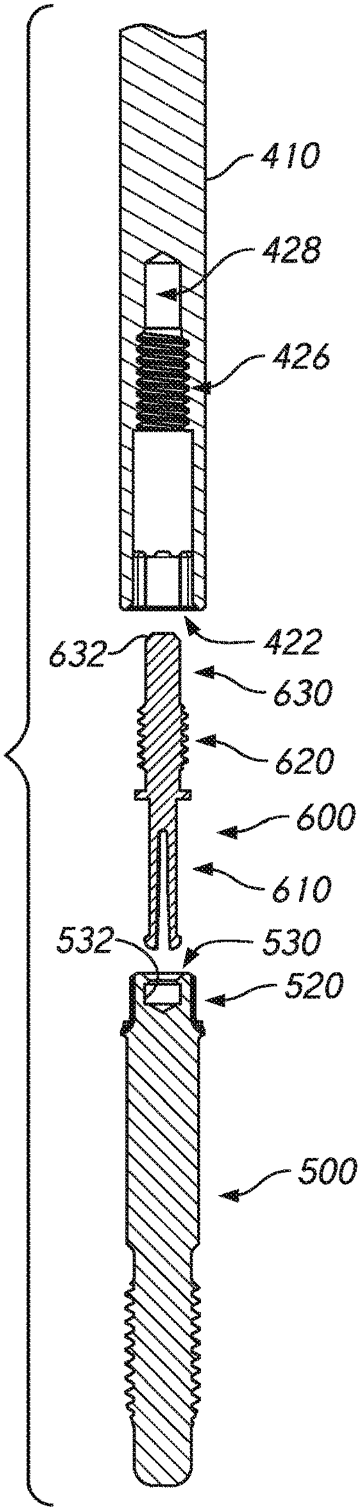
FIG. 8B is an exploded cross-sectional side view of the drive instrument assembly and locking member of FIG. 8A in accordance with embodiments of the present technology.

FIG. 7 is a side view of the drive instrument assembly 400 (handle not shown) and locking member 500. FIG. 8A is a cross-sectional view of the drive instrument assembly 400, locking member 500, and connecting member 600 taken along line 8A-8A of FIG. 7. FIG. 8B is an exploded view of the side cross-sectional view of FIG. 8A. A description of the drive instrument assembly 400 and locking member 500 discussed in connection with FIGS. 3A-6 applies equally to FIGS. 7-8B unless indicated otherwise.

Referring to FIG. 8B, the drive head 520 can include a pocket 530 (which can also be referred to as a chamber, a recessed area, or the like). The spring element 610 can be at least partially insertable into the pocket 530 of the drive head 520. The pocket 530 can additionally include an undercut 532 (e.g., an inner flange, an inner rim, a flared end, a narrowed portion, etc.) configured to releasably receive at least part of the spring element 610. When inserted within the pocket 530 and biased outwardly, at least part of the spring element 610 can contact or abut the undercut 532 to releasably couple the locking member 500 to the connecting member 600.

The spring element 610 can be released from the drive head 520 and/or the pocket 530 by applying a proximal force to the drive instrument assembly 400. The proximal force can cause the spring element 610 to compress such that the spring element 610 can be removed from the pocket 530 and uncouple/release the drive head 520 of the locking member 500. Applying a proximal force to the drive instrument assembly 400 can uncouple the locking member 500 while the locking member is threadably engaged with an intervertebral spacer (e.g., the spacer 300 of FIGS. 3C-3D).

The connecting member 600 can be releasably received by the drive shaft 410. For example, the connecting member 600 can include a threaded region 620, and the socket 422 can include a corresponding threaded region 426 configured to threadably hold/mate with the threaded region 620 to couple the connecting member to the delivery instrument 400 when the connecting member 600 is inserted within the socket 422. The connecting member 600 can further include an end portion 630 positioned distally from the threaded region 620. The end portion 630 can correspond to an end chamber 428 of the socket 422, and can include an end taper 632. The end taper 632 and end portion 630 can have a width less than the threaded region 620 so that the connecting member 600 can be insertable into the socket 422. In some embodiments, the threaded region 426 can be modular such that one or more other connecting members can be coupled to the delivery instrument, each of which can be configured to couple to other drive screws, locking members, and the like. Accordingly, the delivery instrument 400 can to be used with a wide range of different locking member, drive screws, and/or implants.

In some embodiments, the connecting member can be included in an implant kit, for example, along with a corresponding implant and/or locking screw(s) (each of which can provide for a different amount of expansion of the implant). The drive shaft 410 and/or the connecting member 600 can be disposable or reusable and may be included in the kit or in a separate delivery instrument kit.

In an alternate embodiment, the connecting member 600 can be an integral component of the drive shaft 410. For example, the retention mechanism 420 can be a one-piece component that includes the socket 422, the interior grooves 424, and the spring element 610. The retention mechanism 420 can be configured to releasably receive at least a portion of the drive head 520, and the spring element 610 can be at least partially insertable within the pocket 530 of the drive head 520 to releasably hold the locking member 500 to the drive instrument assembly 400.

In some embodiments, the drive shaft 410 can include an assembly of multiple shafts. For example, the drive shaft 410 can include an outer shaft and an inner shaft slidably disposed within the outer shaft. The outer shaft can define the socket 422 and can at least partially contain the drive head 520 of the locking member 500. The inner shaft can include the threaded region 426, the end chamber 428, and be threadably coupled to the connecting member 600. The inner shaft can be moved axially (e.g., proximally and/or distally) to translate the connecting member 600 relative to the outer shaft. This can allow the spring element 610 of the connecting member 600 to be selectively inserted into and/or decoupled from the drive head 520 while the drive head 520 remains stationary with respect to the socket 422 (e.g., drive head 520 can be decoupled from the inner shaft while remaining at least partially contained by outer shaft). In another embodiment, the inner shaft and the connecting member 600 can be a one-piece component. The number and configuration of components of the drive shaft 410 can be selected based on the desired engagement and disengagement with the drive head 520.

Figure 9:
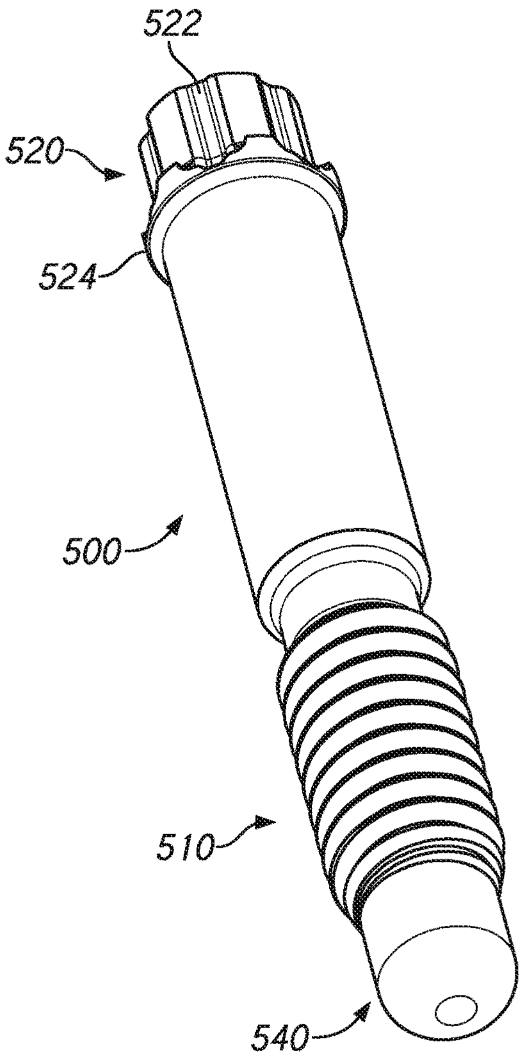
FIG. 9 is an isometric view of the locking member of FIG. 4 in accordance with embodiments of the present technology.
Figure 10:
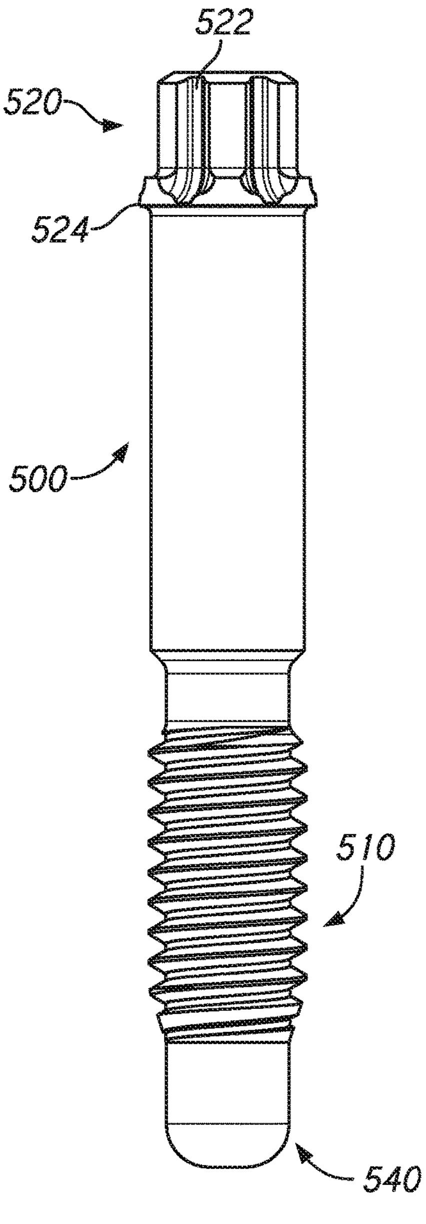
FIG. 10 is a side view of the locking member of FIG. 9.
Figure 11:
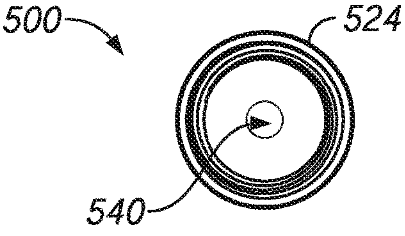
FIG. 11 is a front view of the locking member of FIG. 9.
Figure 12:
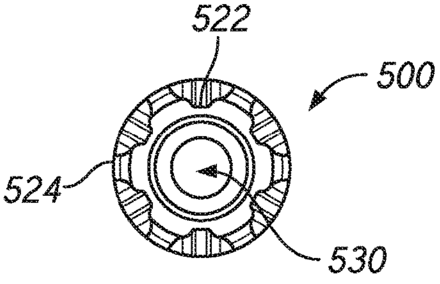
FIG. 12 is an back view of the locking member of FIG. 9.

FIGS. 9-12 illustrate various views of the locking member 500. FIG. 9 is an isometric view of the locking member 500. FIG. 10 is a side view of the locking member 500. FIG. 11 is a front view of the locking member 500. FIG. 12 is an end view of the locking member 500. A description of the locking member 500 discussed in connection with FIGS. 3A-8B applies equally to the locking member 500 of FIGS. 9-12 unless indicated otherwise. Similarly, features of the locking member 500 discussed in connection with FIGS. 9-12 can apply equally to the locking member 500 of FIGS. 3A-8B.

Referring to FIGS. 9-12, the drive head 520 of the locking member 500 can further include an outer annular flange 524. The flange 524 and the threaded region 510 can be configured to lock an intervertebral spacer (e.g., intervertebral spacer 300 of FIGS. 3A-3D) in a horizontally expanded configuration (e.g., FIG. 3B) and/or a vertically expanded configuration (e.g., FIG. 3C). For example, the flange 524 can abut the second end body 320 of FIGS. 3A-3D and the threaded region 510 can threadably engage the first end body 318 of FIGS. 3A-3D. Rotating the drive head 520 can threadably engage the threaded region 510 with the first end body 318 and cause the flange 524 to move the second end body 320 toward the first end body 318, for example, to horizontally and/or vertically expand the intervertebral spacer 300, as described in detail with reference to FIGS. 3A-3D. The locking member 500 can further include a head 540 positioned distally from the threaded region 510. The head 540 can be at least partially rounded to allow for easier insertion into an intervertebral spacer (e.g., the intervertebral spacer 300 of FIGS. 3A-3D, or any other suitable intervertebral spacer).

Figure 13:
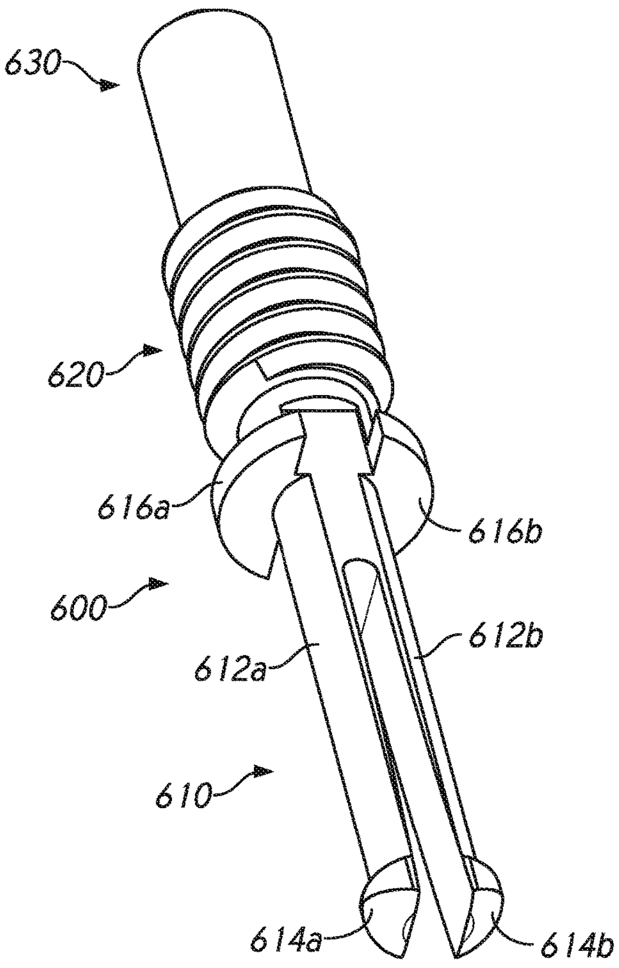
FIG. 13 is an isometric view of the connecting member of FIG. 5 in accordance with embodiments of the present technology.
Figure 14:
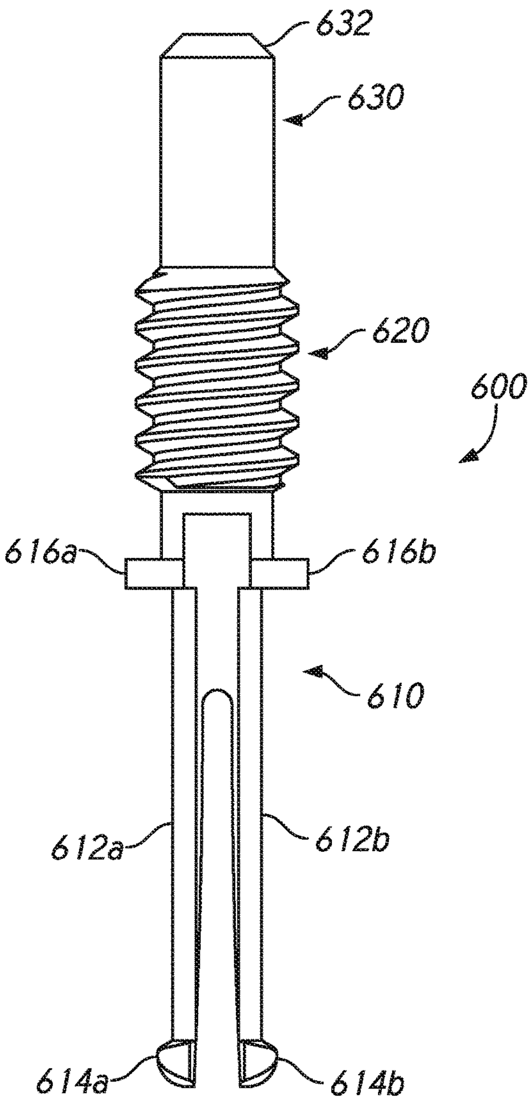
FIG. 14 is a side view of the connecting member of FIG. 13.
Figure 15:
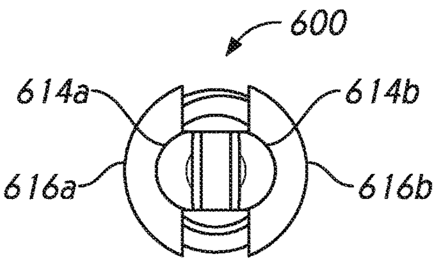
FIG. 15 is a front view of the connecting member of FIG. 13.

FIGS. 13-15 illustrate various views of the connecting member. FIG. 13 is an isometric view of the connecting member 600. FIG. 14 is a side view of the connecting member 600. FIG. 15 is a front view of the connecting member 600. A description of the connecting member 600 discussed in connection with FIGS. 5-8B applies equally to the connecting member 600 unless indicated otherwise. Similarly, features of the connecting member 600 discussed in connection with FIGS. 13-15 can apply equally to the connecting member 600 of FIGS. 5-8B.

Referring to FIGS. 13-15, the spring element 610 can be a cantilever spring having a plurality of outwardly biased arms 612*a*-*b*, and each of the arms 612*a*-*b* can include a corresponding end prong 614*a*-*b*. Referring to FIGS. 13 and 14, the arms 612*a*-*b* and the corresponding prongs 614*a*-*b* can be insertable into a female feature (e.g., pocket 530 of the drive head 520 of FIG. 8B) to releasably hold a male feature, such as a drive head (e.g., drive head 520 in the socket 422 of FIG. 8B). Additionally, the prongs 614*a*-*b* and/or the arms 612*a*-*b* can correspond to an undercut (such as the undercut 532 of FIG. 8B) to releasably couple the spring element to a drive head, as discussed in connection with the pocket 530 of the drive head 520 of FIG. 8B.

Referring again to FIGS. 13-15, the connecting member 600 can further include a plurality of ridges or flanges 616*a*-*b*. Each of the ridges 616*a*-*b* can be positioned proximally from and/or at least partially aligned with one of the arms 612*a*-*b* of the spring element 610. Referring additionally to FIG. 8B, the ridges 616*a*-*b* can have a width greater than the width of the threaded region 620 and/or the threaded region 426 of the socket 422 to limit the extent to which the connecting member 600 can be inserted into socket 422.

Figures 16A, 16B, 16C, 17, 18:
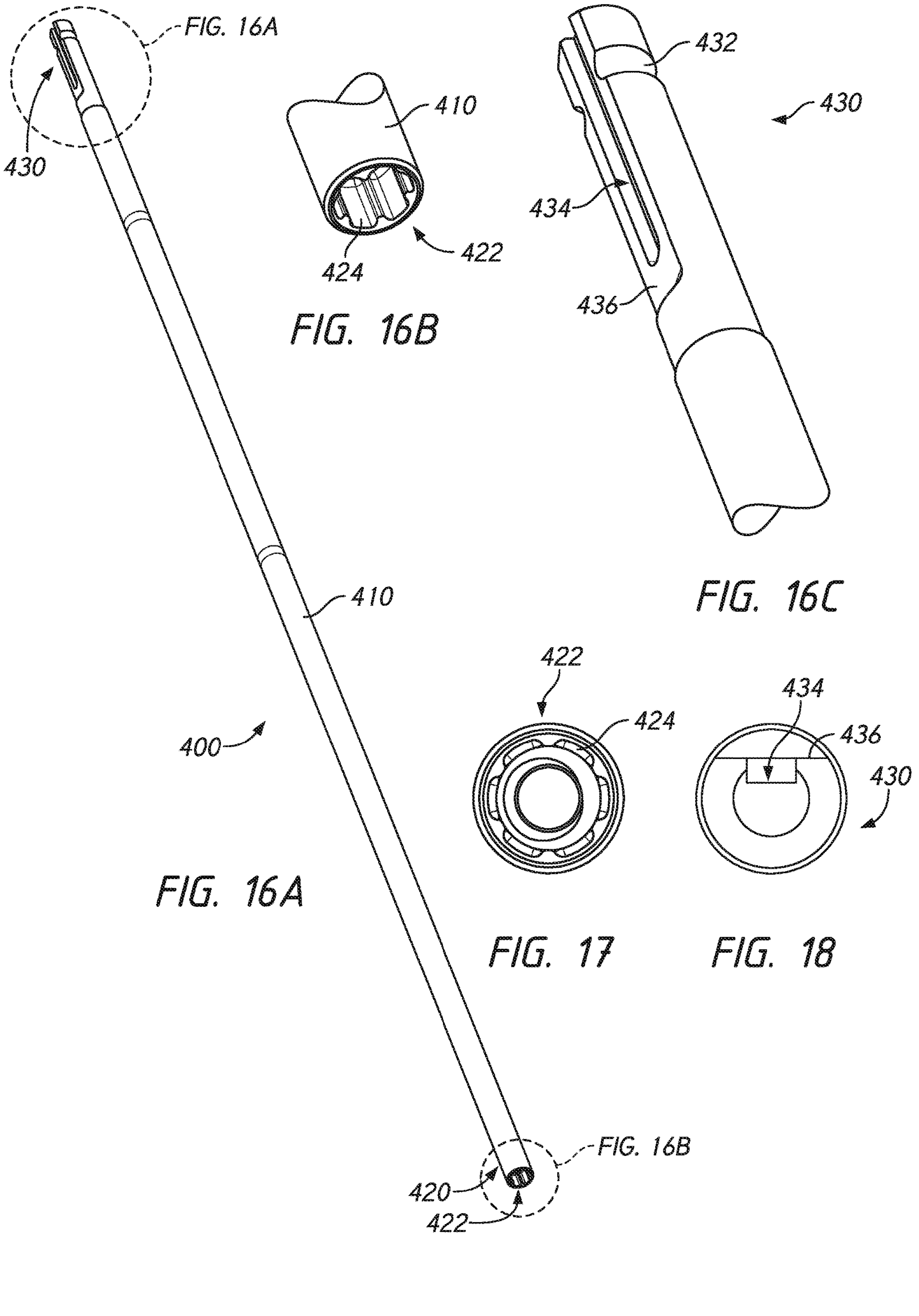
FIG. 16A is an isometric view of the drive instrument assembly of FIG. 4 in accordance with embodiments of the present technology.
FIG. 16B is a detailed isometric view of a socket of the drive instrument assembly of FIG. 16A in accordance with embodiments of the present technology.
FIG. 16C is a detailed isometric view of a connecting region of the drive instrument assembly of FIG. 16A in accordance with embodiments of the present technology.
FIG. 17 is a front view of the drive instrument assembly of FIG. 16A in accordance with embodiments of the present technology.
FIG. 18 is a back view of the drive instrument assembly of FIG. 16A in accordance with embodiments of the present technology.

FIGS. 16A-18 illustrate various views of the drive instrument assembly 400. FIG. 16A is an isometric view of the drive instrument assembly 400. FIG. 16B is a detailed isometric view of the socket 422 of the drive instrument assembly 400. FIG. 16C is a detailed isometric view of the connecting region 430 of the drive instrument assembly 400. FIG. 17 is a front view of the socket 422. FIG. 18 is an end view of the connecting region 430. Referring to FIGS. 16A-18 together, in some embodiments, the drive instrument assembly 400 can include at least some aspects that are generally similar or identical in structure and/or function to the instrument 110 of FIG. 1 and/or the instrument 210 of FIGS. 2A and 2B. In other embodiments, the drive instrument assembly 400 can be coupled to the instrument 110 of FIG. 1, the instrument 210 of FIGS. 2A and 2B, and/or the drive assembly 216 of FIGS. 2A and 2B.

Referring to FIGS. 16A, 16C, and 18 the connecting region 430 can be connected by a handle (e.g., the handle 440 of FIG. 5) and used to manipulate the drive instrument assembly 400 and/or a locking member, such as the locking member 500 of FIGS. 4A-12. The connecting region 430 can include an axial or radial groove 432 extending at least partially about/around a longitudinal axis of the delivery instrument 400, a longitudinal groove 434 extending in a direction at least generally parallel to the longitudinal axis of the delivery instrument, and a locking surface 436. The axial groove 432 can be releasably received by a handle or another instrument (e.g., the instrument 110 of FIG. 1, the instrument 210 of FIG. 210, etc.) to couple the drive instrument assembly 400 to the instrument. Additionally, the locking surface 436 and/or the longitudinal groove 434 can rotationally fix the drive instrument assembly 400 relative to another instrument so that said instrument can be used to rotate the drive instrument assembly 400. In some embodiments the connecting region 430 can be directly coupled to the handle assembly 212 of FIG. 2A or the elongated body 214 of FIG. 2A.

Referring to FIGS. 16A-16B, in the illustrated embodiment, the drive shaft 410 has a circular cross-sectional shape. In other embodiments, the drive shaft 410 can have a triangular, square, pentagonal, hexagonal, or any other suitable cross-sectional shape. Referring additionally to FIG. 17, while the socket 422 is shown to have interior grooves 424 in a hexagonal configuration, in other embodiments the interior grooves 424 can be in a triangular, square, pentagonal, heptagonal, octagonal, or any other suitable configuration.

Figure 19:
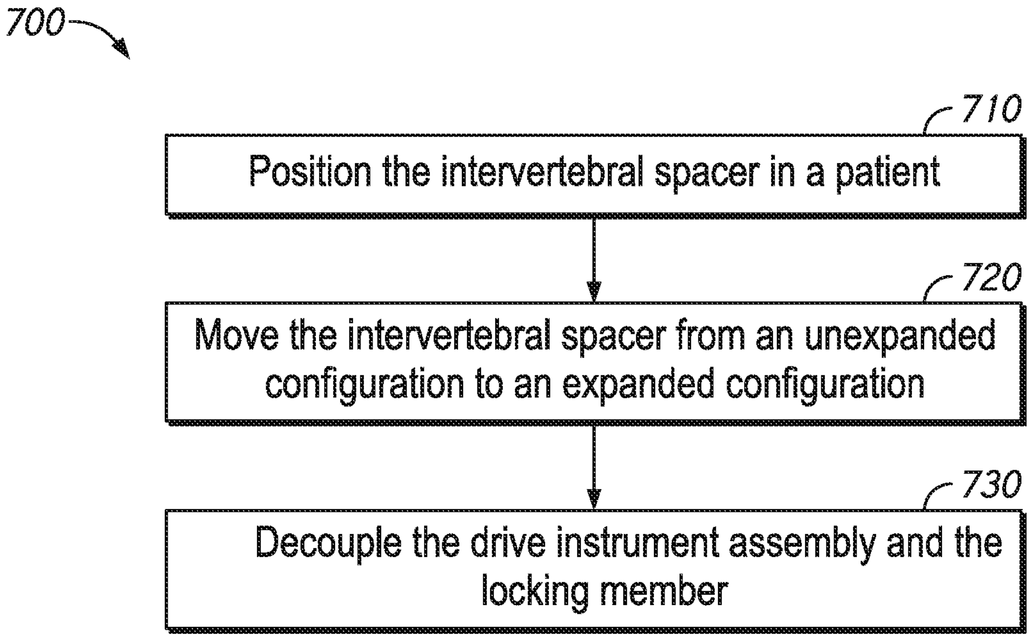
FIG. 19 is a flow chart of a method for locking a configuration of an intervertebral spacer implanted between first and second vertebral bodies of a spine of a subject in accordance with embodiments of the present technology.

FIG. 19 is flow diagram of a method 700 of implanting a device, for example, between first and second vertebral bodies of a spine of a subject. The method can be used with any embodiments of the present technology described herein and/or with one or more components thereof (e.g., system 100 of FIG. 1, instrument 210 of FIGS. 2A and 2B, intervertebral spacer 300 of FIGS. 3A-3D, drive instrument assembly 400, locking member 500, connecting member 600, etc.).

At block 710, the method includes positioning the intervertebral spacer in the patient by, for example, aligning the locking member with an opening or port of an intervertebral spacer within the patient or outside the patient and coupling the locking member to the drive instrument. The drive instrument can be used to insert the locking member into the patient when the locking member is coupled to the intervertebral spacer. The drive instrument assembly can include a socket configured to receive at least a portion of a drive head of the locking member. The socket can be further configured to rotationally fix the locking member with respect to the drive instrument assembly. The drive instrument assembly can further include a spring element biased outwardly to releasably hold the drive head in the socket when the spring element extends into the drive head.

At block 720, the method includes moving the intervertebral spacer from an unexpanded configuration and an expanded configuration. The intervertebral spacer can be expandable in a horizontal direction (e.g., into a horizontally expanded configuration) and/or a vertical direction (e.g., into a vertically expanded configuration). The intervertebral spacer can be expanded by using the drive instrument assembly to drive the locking member. For example, rotating the drive instrument assembly can cause corresponding rotation of the locking member, which can cause the intervertebral spacer to expand horizontally and/or vertically. Expanding the intervertebral spacer can bring one or more surfaces (e.g., upper surface 310, lower surface 312, first side 114, and/or second side 116 of FIG. 3A) of the intervertebral spacer into contact with at least one vertebral endplate of the spine of the subject.

At block 730, the method includes decoupling the drive instrument assembly and the locking member. Decoupling the drive instrument assembly and the locking member can lock the intervertebral spacer in a horizontally and/or vertically expanded configuration. A proximal force can be applied to the drive instrument assembly to decouple the locking member. The proximal force can cause the spring element of the drive instrument assembly to compress such that the spring element exits the pocket, thereby uncoupling the drive head of the locking member. The drive instrument assembly can further include a connecting member, the connecting member can include the spring element, and the proximal force can uncouple the connecting member from the locking member. In some embodiments, the drive instrument assembly can include an inner shaft having the spring element, the inner shaft being disposed within an outer shaft having the socket. The proximal force can be applied to the inner shaft to move the inner shaft proximally relative to the outer shaft and decouple the spring element from the locking member.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, the actions of method 700 can be interchanged with one another or interchanged with other actions disclosed herein.

EXAMPLES

Several aspects of the present technology are set forth in the following examples:

1. A system for treating a spine of a subject, the system comprising:
   - an intervertebral spacer configured to be implanted between a first and a second vertebra of the spine of the subject, wherein the intervertebral spacer is movable between an unexpanded configuration and an expanded configuration;
   - a locking member including:
     - a threaded distal region configured to threadably engage the intervertebral spacer, and
     - a proximal drive head; and
   - a drive instrument assembly configured to rotate the locking member to move the intervertebral spacer from the unexpanded configuration to the expanded configuration, the drive instrument assembly including a retention mechanism detachably couplable to the locking member, the retention mechanism including:
     - a socket configured to receive the drive head to rotationally fix the drive instrument assembly to the locking member, and
     - a spring element biased outwardly to releasably hold the drive head in the socket when the spring element extends into the drive head.

2. The system of example 1 wherein the spring element is a multi-pronged-pronged cantilever spring.

3. The system of example 1 or example 2 wherein the drive head includes a pocket having an undercut opening, and wherein the pocket and the undercut are configured to releasably receive the spring element.

4. The system of example 3 wherein the spring element includes prongs that are biased outwardly to releasably hold the locking member when the prongs are positioned within the pocket of the drive head.

5. The system of any of examples 1-4 wherein the drive head is configured to compress the spring element when the spring element is pulled proximally relative to the drive head.

6. The system of any of examples 1-5 wherein the drive head is configured to compress the spring element when the spring element is moved distally into an opening of the drive head to releasably couple the spring element to the drive head.

7. The system of any of examples 1-6 wherein the drive instrument assembly further includes a drive shaft having the socket, wherein at least a portion of the socket is threadably coupled to a connecting member including the spring element.

8. The system of example 7 wherein the connecting member is configured to retain the drive head such that the drive head is seated in the socket.

9. An instrument assembly operable to move an implantable spacer between a collapsed configuration and an expanded configuration, the instrument assembly comprising:
   - a drive instrument including a socket having a threaded portion;
   - a connecting member having an elongate body positionable within the socket, wherein the connecting member includes—
     - a proximal region threadably coupled to the threaded portion of the drive instrument, and
     - a distal region having a multi-pronged cantilever spring; and
   - a locking member including—
     - a proximal drive head configured to be positioned at least partially within the socket, wherein the proximal drive head includes an end pocket configured to releasably receive at least a portion of the multi-pronged cantilever spring of the connecting member, and
     - a distal threaded portion insertable into the intervertebral spacer;
   - wherein the locking member is configured to keep the intervertebral spacer in the expanded configuration.

10. The instrument assembly of example 9 wherein the proximal drive head includes a pocket having an undercut opening, and wherein the pocket and the undercut are configured to releasably receive at least part of the multi-pronged cantilever spring of the connecting member.

11. The instrument assembly of example 9 or example 10 wherein the multi-pronged cantilever spring includes one or more arms that are biased outwardly to releasably couple the locking member to the drive head.

12. The instrument assembly of any of examples 9-11 wherein the proximal drive head is configured to inwardly deflect the multi-pronged cantilever spring when the multi-pronged cantilever spring is pulled away from the drive head to decouple the locking member from the connecting member.

13. The instrument assembly of any of examples 9-12 wherein the proximal drive head is configured to inwardly deflect the multi-pronged cantilever spring when the multi-pronged cantilever spring is moved into contact with the end pocket of the proximal drive head to releasably couple the multi-pronged cantilever spring to the drive head.

14. A method of implanting a device by locking a configuration of an intervertebral spacer implanted between first and second vertebral bodies of a spine of a subject, the method comprising:

- coupling a locking member to a drive instrument, wherein the drive instrument includes:
  - a socket configured to receive at least a portion of a drive head of the locking member to rotationally fix the drive instrument to the locking member, and
  - a spring element biased outwardly to releasably hold the drive head in the socket when the spring element extends into the drive head;
- coupling the locking member to the intervertebral spacer;
- positioning the intervertebral spacer proximate a target implant location within the subject;
- transitioning the intervertebral spacer from an unexpanded configuration to an expanded configuration; and
- applying a proximal force to the drive instrument to decouple the drive instrument and the locking member.

15. The method of example 14 wherein coupling the locking member to the intervertebral spacer includes rotating the locking member relative to the intervertebral spacer such that a threaded coupling region of the locking member is threadably received by a correspondingly threaded coupling region of the intervertebral spacer.

16. The method of example 14 or example 15 wherein coupling the locking member to the intervertebral spacer includes positioning at least part of the locking member within the intervertebral spacer via a port of the intervertebral spacer configured to releasably receive the locking member.

17. The method of any of examples 14-16 wherein coupling the locking member to the intervertebral spacer includes coupling the locking member to the intervertebral spacer after the intervertebral spacer is positioned proximate the target implant location.

18. The method of any of examples 14-17 wherein transitioning the intervertebral spacer from the unexpanded configuration to the expanded configuration includes rotating the locking member relative to the intervertebral spacer to cause the intervertebral spacer to transition from the unexpanded configuration to the expanded configuration.

19. The method of example 18 wherein rotating the locking member includes rotating the drive instrument to cause the locking member to rotate relative to the intervertebral spacer.

20. The method of any of examples 14-19 wherein transitioning the intervertebral spacer from the unexpanded configured to the expanded configuration includes transitioning the intervertebral spacer to a horizontally expanded configuration.

21. The method of any of examples 14-20 wherein transitioning the intervertebral spacer from the unexpanded configuration to the expanded configuration includes transitioning the intervertebral spacer to a vertically expanded configuration.

22. The method of any of examples 14-21 wherein transitioning the intervertebral spacer from the unexpanded configuration to the expanded configuration includes transitioning the intervertebral spacer to a horizontally and vertically expanded configuration.

23. The method of any of examples 14-22 wherein coupling the locking member to the drive instrument includes positioning at least part of the drive head of the locking member within the socket of the drive instrument to cause at least part of the spring element to be inserted within a chamber defined by the drive head.

24. The method of any of examples 14-23, further comprising coupling a connecting member to the drive instrument, wherein the connecting member includes the spring element and a coupling region opposite the spring element, and wherein the coupling region is configured to be received within the socket to couple the connecting member to the drive instrument, such that coupling the connecting member to the drive instrument includes inserting the coupling region into the socket.

25. A system comprising:

- a screwdriver including a drive shaft and a retention mechanism, the retention mechanism having a socket and a gripper extending through a passage of the socket; and
- a screw including a body and a head, wherein the head includes a receiving pocket configured to receive at least a portion of the gripper such that the retention mechanism detachably holds the head, which is rotationally fixed to the screwdriver.

26. The system of example 25, wherein the gripper clips into an undercut along the receiving pocket to retain the head.

27. The system of example 25 or example 26, wherein the gripper and socket hold the head translationally fixed.

28. The system of any of examples 25-27, wherein the exterior of the head is geometrically congruent to an interior of the socket.

29. The system of any of examples 25-28, wherein the socket is a polygonal socket.

30. The system of any of examples 25-29, wherein the gripper is biased radially outward from a long axis of the drive shaft to press against a sidewall of the head when the gripper is within the receiving pocket.

31. The system of any of examples 25-30, wherein the gripper includes one or more springs.

32. An intervertebral device delivery assembly, comprising:

- an intervertebral device configured to be positioned in a target intervertebral implant location within a patient's spine, wherein the intervertebral device is expandable from a first configuration toward a second configuration;
- a locking member, wherein the locking member includes a threaded region configured to be threadably received by the intervertebral device and a drive head opposite the threaded locking region;
- a connecting member, wherein the connecting member includes (i) a spring element configured to be releasably couplable to the drive head of the locking member and (ii) a threaded coupling region opposite the spring element; and
- a drive instrument, wherein the drive instrument includes a socket configured to threadably receive the threaded coupling region of the connecting member to hold the connecting member at least partially within the socket.

33. The intervertebral device delivery assembly of example 32 wherein the socket is configured to rotationally fix the locking member relative to the drive instrument such that rotation of the drive instrument produces corresponding rotation of the locking member.

34. The intervertebral device delivery assembly of example 32 or example 33 wherein the intervertebral device is configured to transition between the first configuration and the second configuration in response to rotation of the locking member.

35. The intervertebral device delivery assembly of any of examples 32-34 wherein, when the intervertebral device is in the second configuration, the locking member is configured to at least partially prevent the intervertebral device from transitioning toward the first configuration.

36. The intervertebral device delivery assembly of any of examples 32-35 wherein the intervertebral device includes a first end body and a second end body opposite the first end body, wherein the first end body is configured to threadably receive the threaded region of the locking member, wherein the locking member further includes an outer flange configured to abut the second end body when the threaded region is threadably received by the first end body, and wherein rotation of the locking member drives the outer flange and the second end body toward the first end body to transition the intervertebral device from the first configuration toward the second configuration.

37. A method of implanting an intervertebral device, the method comprising:
- rotating a delivery instrument coupled to a locking member to cause a corresponding rotation of the locking member, wherein the locking member is coupled to an intervertebral device, and wherein rotating the locking member includes changing a configuration of the intervertebral device; and
- moving the delivery instrument away from the intervertebral device to decouple the delivery instrument from the locking member.

38. A system for treating a spine of a subject, the system comprising:
- an intervertebral device configuration locking member; and
- an intervertebral device delivery instrument configured to be releasably coupled to the intervertebral device configuration locking member.

39. A system for treating a spine of a subject, the system comprising:
- a locking member including a drive head defining a chamber; and
- a delivery instrument including—
  - an outer shaft defining a lumen therethrough, wherein the outer shaft includes a distal end portion defining a keyed socket configured to releasably receive at least part of the drive head; and
  - an inner shaft slidably disposed within the outer shaft, wherein the inner shaft includes a coupling element configured to be at least partially insertable within the chamber of the drive head;
  - wherein the delivery instrument is transitionable between (i) a first configuration, in which the delivery instrument is coupled to the locking member, and (i) a second configuration, in which the locking member is released from the delivery instrument in response to movement of the inner shaft relative to the outer shaft.

40. The system of example 39 wherein the coupling element includes a cantilevered spring arm.

The drive instrument assemblies disclosed herein can be used with non-expandable devices (e.g., screws, cages, etc.), expandable devices (e.g., expandable implants), or other devices. For example, the drive instrument assemblies can be used with devices for reducing nerve compression, maintaining height of the spine or spine segment, and/or restoring stability to the spine. The drive instrument assemblies can also be used in non-medical applications. For example, the drive instrument assemblies can be used to rotate bolts, screws (e.g., locking screws, bone fixation screws, etc.), or other rotatable elements configured to engage the retention mechanism.

Furthermore, the skilled artisan will recognize the interchangeability of various features from different embodiments disclosed herein and disclosed in U.S. Provisional Patent Application No. 63/159,327; U.S. application Ser. No. 16/687,520; App. No. PCT/US20/49982; U.S. Pat. Nos. 10,105,238; 10,201,431; and U.S. Provisional App. No. 63/126,253. For example, the systems, instruments, devices, etc., of U.S. application Ser. No. 16/687,520; App. No. PCT/US20/49982; U.S. Pat. No. 10,105,238; and U.S. Provisional App. No. 63/126,253 can be incorporated into or used with the technology disclosed herein. For example, the locking screws disclosed in U.S. Provisional Application No. 63/126,253 can be configured for use with the drive instrument assemblies disclosed herein. In some examples, components or features of the drive instrument assemblies can be similar to or the same as the inserter instrument and driver as described by U.S. Pat. No. 10,201,431. All of these applications are incorporated herein by reference in their entireties. Similarly, the various features and acts discussed above, as well as other known equivalents for each such feature or act, can be mixed and matched by one of ordinary skill in this art to perform methods in accordance with principles described herein. All of the above cited applications and patents are herein incorporated by reference in their entireties.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A system for treating a spine of a subject, the system comprising:
- an intervertebral spacer configured to be implanted between a first and a second vertebra of the spine of the subject, wherein the intervertebral spacer is movable between an unexpanded configuration and an expanded configuration;
- a locking member including:
  - a threaded distal region configured to threadably engage the intervertebral spacer, and
  - a proximal drive head; and
- a drive instrument assembly configured to rotate the locking member to move the intervertebral spacer from the unexpanded configuration to the expanded configuration, the drive instrument assembly including a retention mechanism detachably couplable to the locking member, the retention mechanism including:
  - a socket configured to receive the drive head to rotationally fix the drive instrument assembly to the locking member, and
  - a spring element biased outwardly to releasably hold the drive head in the socket when the spring element extends into the drive head.

2. The system of claim 1, wherein the spring element is a multi-pronged-pronged cantilever spring.

3. The system of claim 1, wherein the drive head includes a pocket having an undercut opening, and wherein the pocket and the undercut are configured to releasably receive the spring element.

4. The system of claim 3, wherein the spring element includes prongs that are biased outwardly to releasably hold the locking member when the prongs are positioned within the pocket of the drive head.

5. The system of claim 1, wherein the drive head is configured to compress the spring element when the spring element is pulled proximally relative to the drive head.

6. The system of claim 1, wherein the drive head is configured to compress the spring element when the spring element is moved distally into an opening of the drive head to releasably couple the spring element to the drive head.

7. The system of claim 1, wherein the drive instrument assembly further includes a drive shaft having the socket, wherein at least a portion of the socket is threadably coupled to a connecting member including the spring element.

8. The system of claim 7, wherein the connecting member is configured to retain the drive head such that the drive head is seated in the socket.

9. The system of claim 1, wherein the drive instrument assembly further including
- an outer shaft defining a lumen therethrough, wherein the outer shaft includes the socket configured to releasably receive the drive head; and
- an inner shaft slidably disposed within the lumen of the outer shaft, wherein the inner shaft includes the spring element configured to releasably hold the drive head.

10. The system of claim 9, wherein the drive instrument assembly is transitionable between (i) a first configuration, in which the drive instrument assembly is coupled to the locking member, and (i) a second configuration, in which the locking member is released from the drive instrument assembly in response to movement of the inner shaft relative to the outer shaft.

11. A system for treating a spine of a patient, the system comprising:
- an intervertebral device configured to be positioned in a target intervertebral implant location along a patient's spine, wherein the intervertebral device is expandable from a first configuration toward a second configuration; and
- an instrument assembly configured to expand the intervertebral device, the instrument assembly including:
  - a locking member including a threaded region configured to be threadably received by the intervertebral device and a drive head opposite the threaded region;
  - a connecting member including
    - a spring element configured to be releasably couplable to the drive head of the locking member, and
    - a threaded coupling region opposite the spring element; and
- a drive instrument movable relative to the intervertebral device to cause the intervertebral device to move toward the second configuration, wherein the drive instrument includes a socket configured to threadably receive the threaded coupling region of the connecting member to hold the connecting member at least partially within the socket.

12. The system of claim 11, wherein the socket is configured to rotationally fix the locking member relative to the drive instrument such that rotation of the drive instrument produces corresponding rotation of the locking member.

13. The system of claim 11, wherein the intervertebral device is configured to transition between the first configuration and the second configuration in response to rotation of the locking member.

14. The system of claim 11, wherein, when the intervertebral device is in the second configuration, the locking member is configured to at least partially prevent the intervertebral device from transitioning toward the first configuration.

15. The system of claim 11, wherein
- the intervertebral device includes a first end body and a second end body opposite the first end body, wherein the first end body is configured to threadably receive the threaded region of the locking member, and
- the locking member further includes an outer flange configured to abut the second end body when the threaded region is threadably received by the first end body, and, wherein rotation of the locking member drives the outer flange and the second end body toward the first end body to transition the intervertebral device from the first configuration toward the second configuration.

* * * * *